US010113190B2

(12) United States Patent
Gerstmeir et al.

(10) Patent No.: US 10,113,190 B2
(45) Date of Patent: Oct. 30, 2018

(54) METHOD FOR PRODUCING L-LEUCINE, L-VALINE, L-ISOLEUCINE, α-KETOISOVALERATE, α-KETO-BETA-METHYLVALERATE, OR α-KETOISOCAPROATE USING RECOMBINANT CORYNEBACTERIA THAT CONTAIN THE ILVBN OPERON WHICH CAN BE INDUCED BY PROPIONATE

(71) Applicant: Evonik Degussa GmbH, Essen (DE)

(72) Inventors: Robert Gerstmeir, Werther (DE); Hugo Ramos-Vera, Bielefeld (DE); Kay Marin, Borgholzhausen (DE)

(73) Assignee: Evonik Degussa GmbH, Essen (DE)

(*) Notice: Subject to any disclaimer, the term of this patent is extended or adjusted under 35 U.S.C. 154(b) by 270 days.

(21) Appl. No.: 14/894,513

(22) PCT Filed: May 23, 2014

(86) PCT No.: PCT/EP2014/060680
§ 371 (c)(1),
(2) Date: Nov. 28, 2015

(87) PCT Pub. No.: WO2014/195154
PCT Pub. Date: Dec. 11, 2014

(65) Prior Publication Data
US 2016/0115506 A1   Apr. 28, 2016

(30) Foreign Application Priority Data

Jun. 3, 2013   (EP) ..................... 13170248

(51) Int. Cl.
| C12P 13/08 | (2006.01) |
| C12N 15/77 | (2006.01) |
| C12P 7/40 | (2006.01) |
| C12P 13/06 | (2006.01) |
| C12N 9/88 | (2006.01) |
| C12N 9/10 | (2006.01) |

(52) U.S. Cl.
CPC ............ *C12P 13/08* (2013.01); *C12N 9/1022* (2013.01); *C12N 9/88* (2013.01); *C12N 15/77* (2013.01); *C12P 7/40* (2013.01); *C12P 13/06* (2013.01); *C12Y 202/01006* (2013.01); *C12Y 401/03* (2013.01)

(58) Field of Classification Search
None
See application file for complete search history.

(56) References Cited

U.S. PATENT DOCUMENTS

| 4,656,135 | A | 4/1987 | Tsuchida et al. |
| 5,188,948 | A | 2/1993 | Katsurada et al. |
| 5,275,940 | A | 1/1994 | Kino et al. |
| 5,294,547 | A | 3/1994 | Tsuchida et al. |
| 5,521,074 | A | 5/1996 | Katsumata et al. |
| 5,756,345 | A | 5/1998 | Camakaris et al. |
| 5,770,409 | A | 6/1998 | Pfefferle et al. |
| 5,827,698 | A | 10/1998 | Kikuchi et al. |
| 5,965,391 | A | 10/1999 | Reinscheid et al. |
| 5,990,350 | A | 11/1999 | Stevens et al. |
| 6,613,545 | B1 | 9/2003 | Kennerknecht et al. |
| 6,841,360 | B2 | 1/2005 | Kennerknecht et al. |
| 7,037,690 | B2 | 5/2006 | Hara et al. |
| 7,138,266 | B2 | 11/2006 | Debabov et al. |
| 7,432,085 | B2 | 10/2008 | Hara et al. |
| 7,968,699 | B2 | 6/2011 | Haefer et al. |
| 8,741,608 | B2 | 6/2014 | Claes et al. |
| 8,912,313 | B2 | 12/2014 | Reth et al. |
| 8,951,759 | B2 | 2/2015 | Claes et al. |
| 9,045,762 | B2 | 6/2015 | Reth et al. |
| 9,074,229 | B2 | 7/2015 | Reth et al. |
| 9,347,048 | B2 | 5/2016 | Gerstmeir et al. |
| 9,879,289 | B2 | 1/2018 | Karau et al. |
| 2004/0014123 | A1 | 1/2004 | Kennerknecht et al. |
| 2008/0268502 | A1 | 10/2008 | Haefer et al. |
| 2013/0004999 | A1 | 1/2013 | Reth et al. |

FOREIGN PATENT DOCUMENTS

| CA | 2299105 | 8/2000 |
| DE | 10110344 A1 | 3/1993 |
| DE | 10128510 A1 * | 12/2002 |
| EP | 0 530 765 | 3/1993 |
| EP | 1 108 790 | 6/2001 |
| EP | 1 491 634 | 12/2004 |
| WO | WO 03/014330 | 2/2003 |
| WO | WO 03/040373 | 5/2003 |
| WO | WO 2004/069996 | 8/2004 |

OTHER PUBLICATIONS

English translation of the International Search Report for corresponding international application PCT/EP2014/060680 filed May 23, 2014.
English language translation of the Written Opinion of the International Searching Authority for corresponding application PCT/EP2014/060680 filed May 23, 2014.
English language translation of the International Preliminary Report on Patentability for corresponding international application PCT/EP2014/060680 filed May 23, 2014.
Amann, et al., "Tightly regulated tac promoter vectors useful for the expression of unfused and fused proteins in *Escherichia coli*," *Gene* 69(2):301-315 (Sep. 1988).
Amann, et al., "ATG vectors for regulated high-level expression of cloned genes in *Escherichia coli*," *Gene* 40(2-3):183-190 (Accepted Sep. 1985).
Claes, et al.,"*Corynebacterium glutamicum* prpDBC2 gene cluster, complete sequence," Database accession No. AF434799 (Apr. 2005).

(Continued)

*Primary Examiner* — Suzanne M Noakes
*Assistant Examiner* — Jae W Lee
(74) *Attorney, Agent, or Firm* — Law Office of Michael A. Sanzo, LLC

(57) ABSTRACT

The invention relates to a process for the production of amino acids and keto acids using microorganisms, in which a promoter inducible by propionate makes possible the regulated expression of certain genes.

12 Claims, 1 Drawing Sheet
Specification includes a Sequence Listing.

(56) References Cited

OTHER PUBLICATIONS

Elišáková, et al., "Feedback-Resistant Acetohydroxy Acid Synthase Increases Valine Production in *Corynebacterium glutamicum*," *Applied and Environmental Microbiology* 71(1):207-213 (Jan. 2005).

Ikeda, et al., "The *Corynebacterium glutamicum* genome: features and impacts on biotechnological processes," *Appl. Microbiol. Biotechnol.* 62:99-109 (Aug. 2003).

Jungwirth, et al., "Triple transcriptional control of the resuscitation promoting factor 2 (rpf2) gene of *Corynebacterium glutamicum* by the regulators of acetate metabolism RamA and RamB and the cAMP-dependent regulator GlxR," *FEMS Microbiol. Lett.* 281(2):190-197 (Apr. 2008).

Kalinowski, et al., "The complete *Corynebacterium glutamicum* ATCC 13032 genome sequence and its impact on the production of L-aspartate-derived amino acids and vitamins," *Journal of Biotechnology* 104(1-3):5-25 (Sep. 2003).

Keilhauser, et al., "Isoleucine Synthesis in *Corynebacterium glutamicum*: Molecular Analysis of the ilvB-ilvN-ilvC Operon," *Journal of Bacteriology* 175(17):5595-5603 (Sep. 1993).

Kirchner, et al., "Tools for genetic engineering in the amino acid-producing bacterium *Corynebacterium glutamicum*," *Journal of Biotechnology* 104(1-3):287-299 (Sep. 2003).

Mendel, et al., "The N-terminal Domain of the Regulatory Subunit is Sufficient for Complete Activation of Acetohydroxyacid Synthase III from *Escherichia coli*," *J. Mol. Biol.* 325(1):275-284 (Jan. 2003).

Pátek, et al., "Promoters of *Corynebacterium glutamicum*," *Journal of Biotechnology* 104(1-3):311-323 (Sep. 2003).

Plassmeir, et al., A propionate-inducible expression system based on the *Corynebacterium glutamicum* prpD2 promoter and PrpR activator and its application for the redirection of amino acid biosynthesis pathways, *Journal of Biotechnology* 163(2):225-232 (Jan. 2013).

Plassmeir, et al., "Molecular characterization of PrpR, the transcriptional activator of propionate catabolism in *Corynebacterium glutamicum*," *Journal of Biotechnology* 159(1-2):1-11 (May 2012).

Srivastava, et al., "Antisense Downregulation of $\sigma^{32}$ as a Transient Metabolic Controller in *Escherichia coli*: Effects on Yield of Active Organophosphorus Hydrolase," *Applied and Environmental Microbiology* 66(10):4366-4371 (Oct. 2000).

Stansen, et al., "Characterization of a *Corynebacterium glutamicum* Lactate Utilization Operon Induced during Temperature-Triggered Glutamate Production," *Applied and Environmental Microbiology* 71(10):5920-5928 (Oct. 2005).

Tauch, et al., "Plasmids in *Corynebacterium glutamicum* and their molecular classification by comparative genomics," *Journal of Biotechnology* 104(1-3):27-40 (Sep. 2003).

Tsuchiya, et al., "Genetic Control Systems of *Escherichia coli* can confer inducible expression of cloned genes in coryneform bacteria," *Bio/Technology* 6:428-431 (Apr. 1988).

Vašicová, et al., "Analysis of the *Corynebacterium glutamicum* dapA Promoter," *Journal of Bacteriology* 181(19):6188-6191 (Oct. 1999).

Wada, et al., "Enhanced Valine Production in *Corynebacterium glutamicum* with Defective $H^+$-ATPase and C-Terminal Truncated Acetohydroxyacid Synthase," *Biosci. Biotechnol. Biochem.* 72(11):2959-2965 (online publication Nov. 2008).

English translation of Office Action for counterpart Russian application 2015156852/10(087608) from correspondence of Mar. 30, 2018.

Russian Search Report for counterpart Russian application 2015156852/10(087608) completed Mar. 30, 2018.

Database EMBL: accession No. AF434799, Corynebacterium glutamicum prpDBC2 gene cluster, complete sequence, Apr. 15, 2005.

* cited by examiner

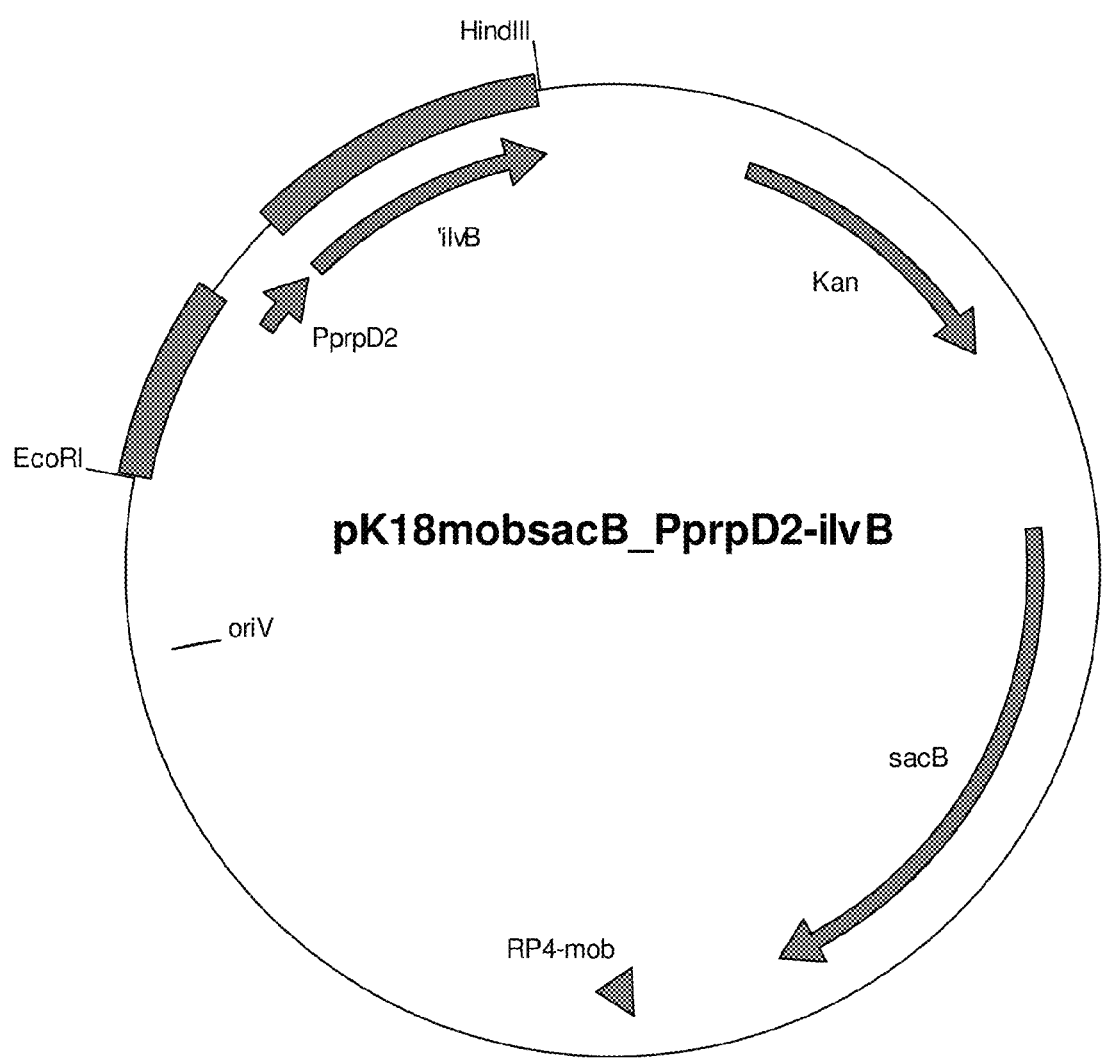

SEQUENCE LISTING

<160> NUMBER OF SEQ ID NOS: 16

<210> SEQ ID NO 1
<211> LENGTH: 177
<212> TYPE: DNA
<213> ORGANISM: Corynebacterium glutamicum
<220> FEATURE:
<221> NAME/KEY: repeat_region
<222> LOCATION: (22)..(49)
<223> OTHER INFORMATION: IR1
<220> FEATURE:
<221> NAME/KEY: repeat_region
<222> LOCATION: (77)..(105)
<223> OTHER INFORMATION: IR2

<400> SEQUENCE: 1
ctccagcgtc cacgaatatg cccccgcgcg ccgggtgggg agcgaaggga accccaagg      60 aattggcgtt gaggtggcga ttttgcatgt tttactcaaa attactttgg tggtcacaaa    120
attacacaac ttttacagtg acctagatcg cttttaaag aattagcgtg gtgtgca        177

<210> SEQ ID NO 2
<211> LENGTH: 177
<212> TYPE: DNA
<213> ORGANISM: Corynebacterium glutamicum
<220> FEATURE:
<221> NAME/KEY: repeat_region
<222> LOCATION: (22)..(49)
<223> OTHER INFORMATION: IR1
<220> FEATURE:
<221> NAME/KEY: repeat_region
<222> LOCATION: (77)..(105)
<223> OTHER INFORMATION: IR2

<400> SEQUENCE: 2

```
ctccagcgtc caagaatatg ccccgcgcg ccgggtgggg agcgaaggga acccccaagg    60
aattggcgtt gaggtggtga ttttgcatgt tttactcaaa atcactttga tggtcacaaa   120
attacacaac ttttacagtg acctacattg ctttttaaag aattagtgtg gtgtgca      177
```

<210> SEQ ID NO 3
<211> LENGTH: 177
<212> TYPE: DNA
<213> ORGANISM: Corynebacterium glutamicum
<220> FEATURE:
<221> NAME/KEY: repeat_region
<222> LOCATION: (22)..(49)
<223> OTHER INFORMATION: IR1
<220> FEATURE:
<221> NAME/KEY: repeat_region
<222> LOCATION: (77)..(105)
<223> OTHER INFORMATION: IR2

<400> SEQUENCE: 3

```
ctccagcgtc caagaatatg ccccgcgcg ccgggtgggg agcgaaggga acccccaagg    60
aattggcgtt gaggtggcga ttttgcatgt tttactcaaa atcactgtga tggtcacaaa   120
attacacaac ttttacagtg acctagatcg ctttttaaag aattagcgtg gtgtgca      177
```

<210> SEQ ID NO 4
<211> LENGTH: 902
<212> TYPE: DNA
<213> ORGANISM: Corynebacterium glutamicum
<220> FEATURE:
<221> NAME/KEY: promoter
<222> LOCATION: (1)..(177)
<223> OTHER INFORMATION: PprpD2
<220> FEATURE:
<221> NAME/KEY: RBS
<222> LOCATION: (178)..(206)
<223> OTHER INFORMATION: gap RBS
<220> FEATURE:
<221> NAME/KEY: misc_feature
<222> LOCATION: (207)..(209)
<223> OTHER INFORMATION: atg-start codon
<220> FEATURE:
<221> NAME/KEY: gene
<222> LOCATION: (207)..(902)
<223> OTHER INFORMATION: ilvB-coding 5'-region

<400> SEQUENCE: 4

```
ctccagcgtc cacgaatatg ccccgcgcg ccgggtgggg agcgaaggga acccccaagg    60
aattggcgtt gaggtggcga ttttgcatgt tttactcaaa attactttgg tggtcacaaa   120
attacacaac ttttacagtg acctagatcg ctttttaaag aattagcgtg gtgtgcatgc   180
atatttatcg cgagaggaga cacaacatga atgtggcagc ttctcaacag cccactcccg   240
ccacggttgc aagccgtggt cgatccgccg ccctgagcg gatgacaggt gcacaggcaa    300
ttgttcgatc gctcgaggag cttaacgccg acatcgtgtt cggtattcct ggtggtgcgg   360
tgctaccggt gtatgacccg ctctattcct ccacaaaggt gcgccacgtc ctggtgcgcc   420
acgagcaggg cgcaggccac gcagcaaccg gctacgcgca ggttactgga cgcgttggcg   480
tctgcattgc aacctctggc ccaggcgcaa ccaacttggt taccccaatc gctgatgcaa   540
acttggactc cgttcccatg gttgccatca ccggccaggt cggaagtggc ctgctgggta   600
ccgatgcttt ccaggaagcc gatatccgcg catcaccat gccagtgacc aagcacaact   660
tcatggtcac cgaccccaac gacattccac aggcattggc tgaggcattc cacctcgcga   720
ttactggtcg ccctggccct gttctggtgg atattcctaa ggatgtccaa aacgctgaat   780
```

```
tggatttcgt ctggccacca aagatcgacc tgccaggcta ccgcccagtt tctactccgc      840
atgctcgaca gattgagcag gctgtcaaac tgatcggtga agccaaaaag ccagtccttt      900
ac                                                                     902
```

```
<210> SEQ ID NO 5
<211> LENGTH: 1390
<212> TYPE: DNA
<213> ORGANISM: Corynebacterium glutamicum
<220> FEATURE:
<221> NAME/KEY: misc_feature
<222> LOCATION: (494)..(521)
<223> OTHER INFORMATION: IR1
<220> FEATURE:
<221> NAME/KEY: misc_feature
<222> LOCATION: (549)..(577)
<223> OTHER INFORMATION: IR2
<220> FEATURE:
<221> NAME/KEY: RBS
<222> LOCATION: (665)..(678)
<223> OTHER INFORMATION: RBS gap
<220> FEATURE:
<221> NAME/KEY: gene
<222> LOCATION: (679)..(1380)
<223> OTHER INFORMATION: ilvB 5'-region
```

<400> SEQUENCE: 5

```
cgaattcgtg caatcgtgcg aattttggtc gcgcgcatgg tgatctcaat gacggtgcct       60
tcgacaacga tgccgttgcc ctcaaaacgc acccagtcac ccacgccgaa ttgcttttcc      120
gtcaggatga aaaatccggc caagaagtcc gcaacaatcg actgcgcacc aaggccaatg      180
gcagctgacg caatggttgc cggaatcgca gcgcccgcga gagagaaacc aaaagcctgc      240
atcgcggaga cggcaagcat gaaaaacgcc acaatttgcg cgatataaac gccaacgcca      300
gcgaacgcga gctggttctt agtggtgtcc gcatcggctg cagactccac tcgccgcttg      360
ataatacgca tggccagtcg gccgatacgt ggaatcaaaa acgccaagac caggataatt      420
gctacatcaa aaccggtatc gacaatccaa ttccacaatg aatagagcaa atctccagcg      480
tccacgaata tgcccccgcg cgccgggtgg ggagcgaagg gaaccccaa ggaattggcg       540 ttgaggtggc gattttgcat gttttactca aaattacttt ggtggtcaca aaattacaca      600
acttttacag tgacctagat cgcttttttaa agaattagcg tggtgtgcat gcatatttat      660
cgcgagagga gacacaacat gaatgtggca gcttctcaac agcccactcc cgccacggtt      720
gcaagccgtg gtcgatccgc cgcccctgag cggatgacag gtgcacaggc aattgttcga      780
tcgctcgagg agcttaacgc cgacatcgtg ttcggtattc ctggtggtgc ggtgctaccg      840
gtgtatgacc cgctctattc ctccacaaag gtgcgccacg tcctggtgcg ccacgagcag      900
ggcgcaggcc acgcagcaac cggctacgcg caggttactg gacgcgttgg cgtctgcatt      960
gcaacctctg gccaggcgc aaccaacttg gttaccccaa tcgctgatgc aaacttggac     1020
tccgttccca tggttgccat caccggccag gtcggaagtg gcctgctggg taccgatgct     1080
ttccaggaag ccgatatccg cggcatcacc atgccagtga ccaagcacaa cttcatggtc     1140
accgacccca cgacattcc acaggcattg gctgaggcat tccacctcgc gattactggt     1200
cgccctggcc ctgttctggt ggatattcct aaggatgtcc aaaacgctga attggatttc     1260
gtctggccac caaagatcga cctgccaggc taccgcccag tttctactcc gcatgctcga     1320
cagattgagc aggctgtcaa actgatcggt gaagccaaaa agccagtcct ttacattggc     1380
ggcaagcttg                                                           1390
```

<210> SEQ ID NO 6
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: test primer 1

<400> SEQUENCE: 6
aaagcctgca tcgcggagac                                              20

<210> SEQ ID NO 7
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: test primer 2

<400> SEQUENCE: 7
tggtgatgcc gcggatatcg                                              20

<210> SEQ ID NO 8
<211> LENGTH: 3411
<212> TYPE: DNA
<213> ORGANISM: Corynebacterium glutamicum
<220> FEATURE:
<221> NAME/KEY: CDS
<222> LOCATION: (500)..(2380)
<223> OTHER INFORMATION: coding region ilvB
<220> FEATURE:
<221> NAME/KEY: CDS
<222> LOCATION: (2394)..(2912)
<223> OTHER INFORMATION: coding region ilvN

<400> SEQUENCE: 8
gtatcgacaa tccaattcca caatgaatag agcaaatatt gaatgggtac gcctaaaatc       60
atgagccaag attagcgctg aaaagtagcg ggagcctgcc tgaactttgt gagaatcctg      120
attccttaac cgaagtgggg gagttttggg ggtgggaatt tcgtgcgtt gtggaattgg       180 aaactcgatg tgtgtagcat gacacaccat gaccattatt cgacttgtag tagtaaccgc      240
gcggcgcctg ccgtaacggc cttccaagtc gtctcgtcaa gcgccctcga caacactcac      300
cacagtgttg gaacgagggc tttcttgttg gttatgaccc aagtagccaa ctttgcaaca      360
gacatctgtc gcactgcgtg cacacgcatc cgcgtcggaa caattttaaa tgagggcttt      420
gtctttaggc tgagttgaaa tcggcttggc ttggacgggt cctgtgaaaa tccttattta      480
gtaaaggagc cagaaagtc gtg aat gtg gca gct tct caa cag ccc act ccc       532
                       Val Asn Val Ala Ala Ser Gln Gln Pro Thr Pro
                         1               5                  10 gcc acg gtt gca agc cgt ggt cga tcc gcc gcc cct gag cgg atg aca        580
Ala Thr Val Ala Ser Arg Gly Arg Ser Ala Ala Pro Glu Arg Met Thr
              15                  20                  25 ggt gca aag gca att gtt cga tcg ctc gag gag ctt aac gcc gac atc        628
Gly Ala Lys Ala Ile Val Arg Ser Leu Glu Glu Leu Asn Ala Asp Ile
 30                  35                  40 gtg ttc ggt att cct ggt ggt gcg gtg cta ccg gtg tat gac ccg ctc        676
Val Phe Gly Ile Pro Gly Gly Ala Val Leu Pro Val Tyr Asp Pro Leu
     45                  50                  55 tat tcc tcc aca aag gtg cgc cac gtc ttg gtg cgc cac gag cag ggc        724
Tyr Ser Ser Thr Lys Val Arg His Val Leu Val Arg His Glu Gln Gly
 60                  65                  70                  75

-continued

| | |
|---|---|
| gca ggc cac gca gca acc ggc tac gcg cag gtt act gga cgc gtt ggc<br>Ala Gly His Ala Ala Thr Gly Tyr Ala Gln Val Thr Gly Arg Val Gly<br>80                           85                         90 | 772 |
| gtc tgc att gca acc tct ggc cca gga gca acc aac ttg gtt acc cca<br>Val Cys Ile Ala Thr Ser Gly Pro Gly Ala Thr Asn Leu Val Thr Pro<br>95                       100                      105 | 820 |
| atc gct gat gca aac ttg gac tcc gtt ccc atg gtt gcc atc acc ggc<br>Ile Ala Asp Ala Asn Leu Asp Ser Val Pro Met Val Ala Ile Thr Gly<br>110                      115                     120 | 868 |
| cag gtc gga agt ggc ctg ctg ggt acc gac gct ttc cag gaa gcc gat<br>Gln Val Gly Ser Gly Leu Leu Gly Thr Asp Ala Phe Gln Glu Ala Asp<br>125                      130                     135 | 916 |
| atc cgc ggc atc acc atg cca gtg acc aag cac aac ttc atg gtc acc<br>Ile Arg Gly Ile Thr Met Pro Val Thr Lys His Asn Phe Met Val Thr<br>140                      145                     150                     155 | 964 |
| aac cct aac gac att cca cag gca ttg gct gag gca ttc cac ctc gcg<br>Asn Pro Asn Asp Ile Pro Gln Ala Leu Ala Glu Ala Phe His Leu Ala<br>160                      165                     170 | 1012 |
| att act ggt cgc cct ggc cct gtt ctg gtg gat att cct aag gat gtc<br>Ile Thr Gly Arg Pro Gly Pro Val Leu Val Asp Ile Pro Lys Asp Val<br>175                      180                     185 | 1060 |
| cag aac gct gaa ttg gat ttc gtc tgg cca cca aag atc gac ctg cca<br>Gln Asn Ala Glu Leu Asp Phe Val Trp Pro Pro Lys Ile Asp Leu Pro<br>190                      195                     200 | 1108 |
| ggc tac cgc cca gtt tca aca cca cat gct cgc cag atc gag cag gca<br>Gly Tyr Arg Pro Val Ser Thr Pro His Ala Arg Gln Ile Glu Gln Ala<br>205                      210                     215 | 1156 |
| gtc aag ctg atc ggt gag gcc aag aag ccc gtc ctt tac gtt ggt ggt<br>Val Lys Leu Ile Gly Glu Ala Lys Lys Pro Val Leu Tyr Val Gly Gly<br>220                      225                     230                     235 | 1204 |
| ggc gta atc aag gct gac gca cac gaa gag ctt cgt gcg ttc gct gag<br>Gly Val Ile Lys Ala Asp Ala His Glu Glu Leu Arg Ala Phe Ala Glu<br>240                      245                     250 | 1252 |
| tac acc ggc atc cca gtt gtc acc acc ttg atg gct ttg ggt act ttc<br>Tyr Thr Gly Ile Pro Val Val Thr Thr Leu Met Ala Leu Gly Thr Phe<br>255                      260                     265 | 1300 |
| cca gag tct cac gag ctg cac atg ggt atg cca ggc atg cat ggc act<br>Pro Glu Ser His Glu Leu His Met Gly Met Pro Gly Met His Gly Thr<br>270                      275                     280 | 1348 |
| gtg tcc gct gtt ggt gca ctg cag cgc agc gac ctg ctg att gct atc<br>Val Ser Ala Val Gly Ala Leu Gln Arg Ser Asp Leu Leu Ile Ala Ile<br>285                      290                     295 | 1396 |
| ggc tcc cgc ttt gat gac cgc gtc acc ggt gac gtt gac acc ttc gcg<br>Gly Ser Arg Phe Asp Asp Arg Val Thr Gly Asp Val Asp Thr Phe Ala<br>300                      305                     310                     315 | 1444 |
| cct gac gcc aag atc att cac gcc gac att gat cct gcc gaa atc ggc<br>Pro Asp Ala Lys Ile Ile His Ala Asp Ile Asp Pro Ala Glu Ile Gly<br>320                      325                     330 | 1492 |
| aag atc aag cag gtt gag gtt cca atc gtg ggc gat gcc cgc gaa gtt<br>Lys Ile Lys Gln Val Glu Val Pro Ile Val Gly Asp Ala Arg Glu Val<br>335                      340                     345 | 1540 |
| ctt gct cgt ctg ctg gaa acc acc aag gca agc aag gca gag acc gag<br>Leu Ala Arg Leu Leu Glu Thr Thr Lys Ala Ser Lys Ala Glu Thr Glu<br>350                      355                     360 | 1588 |
| gac atc tcc gag tgg gtt gac tac ctc aag ggc ctc aag gca cgt ttc<br>Asp Ile Ser Glu Trp Val Asp Tyr Leu Lys Gly Leu Lys Ala Arg Phe<br>365                      370                     375 | 1636 |
| ccg cgt ggc tac gac gag cag cca ggc gat ctg ctg gca cca cag ttt<br>Pro Arg Gly Tyr Asp Glu Gln Pro Gly Asp Leu Leu Ala Pro Gln Phe<br>380                      385                     390                     395 | 1684 |

```
gtc att gaa acc ctg tcc aag gaa gtt ggc ccc gac gca att tac tgc    1732
Val Ile Glu Thr Leu Ser Lys Glu Val Gly Pro Asp Ala Ile Tyr Cys
            400                 405                 410 gcc ggc gtt ggc cag cac caa atg tgg gca gct cag ttc gtt gac ttt    1780
Ala Gly Val Gly Gln His Gln Met Trp Ala Ala Gln Phe Val Asp Phe
            415                 420                 425 gaa aag cca cgc acc tgg ctc aac tcc ggt gga ctg ggc acc atg ggc    1828
Glu Lys Pro Arg Thr Trp Leu Asn Ser Gly Gly Leu Gly Thr Met Gly
            430                 435                 440 tac gca gtt cct gcg gcc ctt gga gca aag gct ggc gca cct gac aag    1876
Tyr Ala Val Pro Ala Ala Leu Gly Ala Lys Ala Gly Ala Pro Asp Lys
            445                 450                 455 gaa gtc tgg gct atc gac ggc gac ggc tgt ttc cag atg acc aac cag    1924
Glu Val Trp Ala Ile Asp Gly Asp Gly Cys Phe Gln Met Thr Asn Gln
460                 465                 470                 475 gaa ctc acc acc gcc gca gtt gaa ggt ttc ccc att aag atc gca cta    1972
Glu Leu Thr Thr Ala Ala Val Glu Gly Phe Pro Ile Lys Ile Ala Leu
            480                 485                 490 atc aac aac gga aac ctg ggc atg gtt cgc caa tgg cag acc cta ttc    2020
Ile Asn Asn Gly Asn Leu Gly Met Val Arg Gln Trp Gln Thr Leu Phe
            495                 500                 505 tat gaa gga cgg tac tca aat act aaa ctt cgt aac cag ggc gag tac    2068
Tyr Glu Gly Arg Tyr Ser Asn Thr Lys Leu Arg Asn Gln Gly Glu Tyr
            510                 515                 520 atg ccc gac ttt gtt acc ctt tct gag gga ctt ggc tgt gtt gcc atc    2116
Met Pro Asp Phe Val Thr Leu Ser Glu Gly Leu Gly Cys Val Ala Ile
            525                 530                 535 cgc gtc acc aaa gcg gag gaa gta ctg cca gcc atc caa aag gct cga    2164
Arg Val Thr Lys Ala Glu Glu Val Leu Pro Ala Ile Gln Lys Ala Arg
540                 545                 550                 555 gag atc aac gac cgc cca gta gtc atc gac ttc atc gtc ggt gaa gac    2212
Glu Ile Asn Asp Arg Pro Val Val Ile Asp Phe Ile Val Gly Glu Asp
            560                 565                 570 gca cag gta tgg cca atg gtg tct gct gga tca tcc aac tcc gat atc    2260
Ala Gln Val Trp Pro Met Val Ser Ala Gly Ser Ser Asn Ser Asp Ile
            575                 580                 585 cag tac gca ctc gga ttg cgc cca ttc ttt gat ggt gat gaa tct gca    2308
Gln Tyr Ala Leu Gly Leu Arg Pro Phe Phe Asp Gly Asp Glu Ser Ala
            590                 595                 600 gca gaa gat cct gcc gac att cac gaa gcc gtc agc gac att gat gcc    2356
Ala Glu Asp Pro Ala Asp Ile His Glu Ala Val Ser Asp Ile Asp Ala
605                 610                 615 gcc gtt gaa tcg acc gag gca taa ggagagaccc aag atg gct aat tct    2405
Ala Val Glu Ser Thr Glu Ala               Met Ala Asn Ser
620                 625                                   630 gac gtc acc cgc cac atc ctg tcc gta ctc gtt cag gac gta gac gga    2453
Asp Val Thr Arg His Ile Leu Ser Val Leu Val Gln Asp Val Asp Gly
            635                 640                 645 atc att tcc cgc gta tca ggt atg ttc acc cga cgc gca ttc aac ctc    2501
Ile Ile Ser Arg Val Ser Gly Met Phe Thr Arg Arg Ala Phe Asn Leu
            650                 655                 660 gtg tcc ctc gtg tct gca aag acc gaa aca cac ggc atc aac cgc atc    2549
Val Ser Leu Val Ser Ala Lys Thr Glu Thr His Gly Ile Asn Arg Ile
            665                 670                 675 acg gtt gtt gtc gac gcc gac gag ctc aac att gag cag atc acc aag    2597
Thr Val Val Val Asp Ala Asp Glu Leu Asn Ile Glu Gln Ile Thr Lys
            680                 685                 690 cag ctc aac aag ctg atc ccc gtg ctc aaa gtc gtg cga ctt gat gaa    2645
Gln Leu Asn Lys Leu Ile Pro Val Leu Lys Val Val Arg Leu Asp Glu
695                 700                 705                 710
```

```
gag acc act atc gcc cgc gca atc atg ctg gtt aag gtc tct gcg gac    2693
Glu Thr Thr Ile Ala Arg Ala Ile Met Leu Val Lys Val Ser Ala Asp
                715                 720                 725 agc acc aac cgt ccg cag atc gtc gac gcc gcg aac atc ttc cgc gcc    2741
Ser Thr Asn Arg Pro Gln Ile Val Asp Ala Ala Asn Ile Phe Arg Ala
            730                 735                 740 cga gtc gtc gac gtg gct cca gac tct gtg gtt att gaa tcc aca ggc    2789
Arg Val Val Asp Val Ala Pro Asp Ser Val Val Ile Glu Ser Thr Gly
        745                 750                 755 acc cca ggc aag ctc cgc gca ctg ctt gac gtg atg gaa cca ttc gga    2837
Thr Pro Gly Lys Leu Arg Ala Leu Leu Asp Val Met Glu Pro Phe Gly
    760                 765                 770 atc cgc gaa ctg atc caa tcc gga cag att gca ctc aac cgc ggt ccg    2885
Ile Arg Glu Leu Ile Gln Ser Gly Gln Ile Ala Leu Asn Arg Gly Pro
775                 780                 785                 790 aag acc atg gct ccg gcc aag atc taa acagcaatta atctgattgc          2932
Lys Thr Met Ala Pro Ala Lys Ile
                795 acctgctgca taaatgtgac tagtcaaaca ccgtctaatt acatgtgtgt ggtagaacaa    2992 taatgtagtt gtctgcccaa gcgagttaaa ctcccacgat ttacagtggg gggcagacat    3052 cttttcacca aaatttttac gaaaggcgag attttctccc atggctattg aactgcttta    3112 tgatgctgac gctgacctct ccttgatcca gggccgtaag gttgccatcg ttggctacgg    3172 ctcccagggc cacgcacact cccagaacct ccgcgattct ggcgttgagg ttgtcattgg    3232 tctgcgcgag ggctccaagt ccgcagagaa ggcaaaggaa gcaggcttcg aggtcaagac    3292 caccgctgag gctgcagctt gggctgacgt catcatgctc ctggctccag acacctccca    3352 ggcagaaatc ttcaccaacg acatcgagcc aaacctgaac gcaggcgacg cactgctgt     3411

<210> SEQ ID NO 9
<211> LENGTH: 626
<212> TYPE: PRT
<213> ORGANISM: Corynebacterium glutamicum

<400> SEQUENCE: 9

Val Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Lys Ala Ile
            20                  25                  30

Val Arg Ser Leu Glu Glu Leu Asn Ala Asp Ile Val Phe Gly Ile Pro
        35                  40                  45

Gly Gly Ala Val Leu Pro Val Tyr Asp Pro Leu Tyr Ser Ser Thr Lys
    50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Thr
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Gln Glu Ala Asp Ile Arg Gly Ile Thr
    130                 135                 140

Met Pro Val Thr Lys His Asn Phe Met Val Thr Asn Pro Asn Asp Ile
145                 150                 155                 160
```

-continued

Pro Gln Ala Leu Ala Glu Ala Phe His Leu Ala Ile Thr Gly Arg Pro
            165                 170                 175

Gly Pro Val Leu Val Asp Ile Pro Lys Asp Val Gln Asn Ala Glu Leu
        180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ala Lys Lys Pro Val Leu Tyr Val Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
        275                 280                 285

Ala Leu Gln Arg Ser Asp Leu Leu Ile Ala Ile Gly Ser Arg Phe Asp
        290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
        355                 360                 365

Val Asp Tyr Leu Lys Gly Leu Lys Ala Arg Phe Pro Arg Gly Tyr Asp
    370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
        435                 440                 445

Ala Leu Gly Ala Lys Ala Gly Ala Pro Asp Lys Glu Val Trp Ala Ile
    450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
        515                 520                 525

Thr Leu Ser Glu Gly Leu Gly Cys Val Ala Ile Arg Val Thr Lys Ala
    530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

```
Met Val Ser Ala Gly Ser Ser Asn Ser Asp Ile Gln Tyr Ala Leu Gly
            580             585                 590

Leu Arg Pro Phe Phe Asp Gly Asp Glu Ser Ala Ala Glu Asp Pro Ala
        595                 600                 605

Asp Ile His Glu Ala Val Ser Asp Ile Asp Ala Ala Val Glu Ser Thr
    610                 615                 620

Glu Ala
625

<210> SEQ ID NO 10
<211> LENGTH: 172
<212> TYPE: PRT
<213> ORGANISM: Corynebacterium glutamicum

<400> SEQUENCE: 10

Met Ala Asn Ser Asp Val Thr Arg His Ile Leu Ser Val Leu Val Gln
1               5                   10                  15

Asp Val Asp Gly Ile Ile Ser Arg Val Ser Gly Met Phe Thr Arg Arg
            20                  25                  30

Ala Phe Asn Leu Val Ser Leu Val Ser Ala Lys Thr Glu Thr His Gly
        35                  40                  45

Ile Asn Arg Ile Thr Val Val Val Asp Ala Asp Glu Leu Asn Ile Glu
    50                  55                  60

Gln Ile Thr Lys Gln Leu Asn Lys Leu Ile Pro Val Leu Lys Val Val
65                  70                  75                  80

Arg Leu Asp Glu Glu Thr Thr Ile Ala Arg Ala Ile Met Leu Val Lys
                85                  90                  95

Val Ser Ala Asp Ser Thr Asn Arg Pro Gln Ile Val Asp Ala Ala Asn
            100                 105                 110

Ile Phe Arg Ala Arg Val Val Asp Val Ala Pro Asp Ser Val Val Ile
        115                 120                 125

Glu Ser Thr Gly Thr Pro Gly Lys Leu Arg Ala Leu Leu Asp Val Met
    130                 135                 140

Glu Pro Phe Gly Ile Arg Glu Leu Ile Gln Ser Gly Gln Ile Ala Leu
145                 150                 155                 160

Asn Arg Gly Pro Lys Thr Met Ala Pro Ala Lys Ile
                165                 170

<210> SEQ ID NO 11
<211> LENGTH: 28
<212> TYPE: DNA
<213> ORGANISM: Corynebacterium glutamicum
<220> FEATURE:
<221> NAME/KEY: repeat_region
<222> LOCATION: (1)..(28)
<223> OTHER INFORMATION: IR1

<400> SEQUENCE: 11
ccccgcgcgc cgggtgggga gcgaaggg                                    28

<210> SEQ ID NO 12
<211> LENGTH: 29
<212> TYPE: DNA
<213> ORGANISM: Corynebacterium glutamicum
<220> FEATURE:
<221> NAME/KEY: repeat_region
<222> LOCATION: (1)..(29)
<223> OTHER INFORMATION: IR2
```

<400> SEQUENCE: 12

```
gcgattttgc atgttttact caaaattac                                             29
```

<210> SEQ ID NO 13
<211> LENGTH: 2619
<212> TYPE: DNA
<213> ORGANISM: Corynebacterium glutamicum
<220> FEATURE:
<221> NAME/KEY: promoter
<222> LOCATION: (1)..(177)
<223> OTHER INFORMATION: PprpD2
<220> FEATURE:
<221> NAME/KEY: RBS
<222> LOCATION: (178)..(206)
<223> OTHER INFORMATION: RBS gap
<220> FEATURE:
<221> NAME/KEY: misc_feature
<222> LOCATION: (207)..(209)
<223> OTHER INFORMATION: atg-start codon
<220> FEATURE:
<221> NAME/KEY: gene
<222> LOCATION: (207)..(2087)
<223> OTHER INFORMATION: coding region ilvB
<220> FEATURE:
<221> NAME/KEY: gene
<222> LOCATION: (2101)..(2619)
<223> OTHER INFORMATION: coding region ilvN

<400> SEQUENCE: 13

```
ctccagcgtc cacgaatatg cccccgcgcg ccgggtgggg agcgaaggga accccccaagg       60 aattggcgtt gaggtggcga ttttgcatgt tttactcaaa attactttgg tggtcacaaa      120
attacacaac ttttacagtg acctagatcg cttttttaaag aattagcgtg gtgtgcatgc      180
atatttatcg cgagaggaga cacaacatga atgtggcagc ttctcaacag cccactcccg      240
ccacggttgc aagccgtggt cgatccgccg ccctgagcg atgacaggt gcacaggcaa        300 ttgttcgatc gctcgaggag cttaacgccg acatcgtgtt cggtattcct ggtggtgcgg      360
tgctaccggt gtatgacccg ctctattcct ccacaaaggt gcgccacgtc ctggtgcgcc      420
acgagcaggg cgcaggccac gcagcaaccg gctacgcgca ggttactgga cgcgttggcg      480
tctgcattgc aacctctggc ccaggcgcaa ccaacttggt taccccaatc gctgatgcaa      540
acttggactc cgttcccatg gttgccatca ccggccaggt cggaagtggc ctgctgggta      600
ccgatgcttt ccaggaagcc gatatccgcg gcatcaccat gccagtgacc aagcacaact      660
tcatggtcac cgaccccaac gacattccac aggcattggc tgaggcattc caccctcgcga     720 ttactggtcg ccctggccct gttctggtgg atattcctaa ggatgtccaa aacgctgaat      780
tggatttcgt ctggccacca aagatcgacc tgccaggcta ccgcccagtt tctactccgc      840
atgctcgaca gattgagcag gctgtcaaac tgatcggtga agccaaaaag ccagtcctt       900 acgttggtgg tggcgtaatc aaggctgacg cacacgaaga gcttcgtgcg ttcgctgagt      960
acaccggcat cccagttgtc accaccttga tggctttggg tactttccca gagtctcacg     1020
agctgcacat gggtatgcca ggcatgcatg gcactgtgtc cgctgttggt gcactgcagc     1080
gcagcgacct gctgattgct atcggctccc gctttgatga ccgcgtcacc ggtgacgttg     1140 acacccttcgc gcctgacgcc aagatcattc acgccgacat tgatcctgcc gaaatcggca     1200
agatcaagca ggttgaggtt ccaatcgtgg gcgatgcccg cgaagttctt gctcgtctgc     1260
tggaaaccac caaggcaagc aaggcagaga ccgaggacat ctccgagtgg gttgactacc     1320
tcaagggcct caaggcacgt ttcccgcgtg gctacgacga gcagccaggc gatctgctgg     1380
caccacagtt tgtcattgaa accctgtcca aggaagttgg ccccgacgca atttactgcg     1440
```

```
ccggcgttgg ccagcaccaa atgtgggcag ctcagttcgt tgactttgaa aagccacgca    1500
cctggctcaa ctccggtgga ctgggcacca tgggctacgc agttcctgcg gcccttggag    1560
caaaggctgg cgcacctgac aaggaagtct gggctatcga cggcgacggc tgtttccaga    1620
tgaccaacca ggaactcacc accgccgcag ttgaaggttt ccccattaag atcgcactaa    1680
tcaacaacgg aaacctgggc atggttcgcc aatggcagac cctattctat gaaggacggt    1740
actcaaatac taaacttcgt aaccagggcg agtacatgcc cgactttgtt acccttcctg    1800
agggacttgg ctgtgttgcc atccgcgtca ccaaagcgga ggaagtactg ccagccatcc    1860
aaaaggctcg agagatcaac gaccgcccag tagtcatcga cttcatcgtc ggtgaagacg    1920
cacaggtatg gccaatggtg tctgctggat catccaactc cgatatccag tacgcactcg    1980
gattgcgccc attctttgat ggtgatgaat ctgcagcaga agatcctgcc gacattcacg    2040
aagccgtcag cgacattgat gccgccgttg aatcgaccga ggcataagga gagacccaag    2100
atggctaatt ctgacgtcac ccgccacatc ctgtccgtac tcgttcagga cgtagacgga    2160
atcatttccc gcgtatcagg tatgttcacc cgacgcgcat tcaacctcgt gtccctcgtg    2220
tctgcaaaga ccgaaacaca cggcatcaac cgcatcacgg ttgttgtcga cgccgacgag    2280
ctcaacattg agcagatcac caagcagctc aacaagctga tccccgtgct caaagtcgtg    2340
cgacttgatg aagagaccac tatcgcccgc gcaatcatgc tggttaaggt ctctgcggac    2400
agcaccaacc gtccgcagat cgtcgacgcc gcgaacatct tccgcgcccg agtcgtcgac    2460
gtggctccag actctgtggt tattgaatcc acaggcaccc caggcaagct ccgcgcactg    2520
cttgacgtga tggaaccatt cggaatccgc gaactgatcc aatccggaca gattgcactc    2580
aaccgcggtc cgaagaccat ggctccggcc aagatctaa                          2619

<210> SEQ ID NO 14
<211> LENGTH: 1421
<212> TYPE: DNA
<213> ORGANISM: Corynebacterium glutamicum
<220> FEATURE:
<221> NAME/KEY: gene
<222> LOCATION: (7)..(636)
<223> OTHER INFORMATION: 3'-region of the iLvB-gene
<220> FEATURE:
<221> NAME/KEY: gene
<222> LOCATION: (650)..(1168)
<223> OTHER INFORMATION: ilvN gene
<220> FEATURE:
<221> NAME/KEY: misc_feature
<222> LOCATION: (707)..(715)
<223> OTHER INFORMATION: mutated gene section

<400> SEQUENCE: 14
gaattccaga tgtgggcagc tcagttcgtt gactttgaaa agccacgcac ctggctcaac      60
tctggcggcc tgggcaccat gggctacgca gttcctgcgg ctcttggagc aaaggctggc     120
gcacctgaca aggaagtctg ggctatcgac ggcgacggct gtttccagat gaccaaccag     180
gaactcacca ccgccgcagt tgaaggtttc cccattaaga tcgcactaat caacaacgga     240
aacctgggca tggttcgcca atggcagacc ctattctatg aaggacggta ctcaaatact     300
aaacttcgta accagggcga gtacatgccc gactttgtta ccctttctga gggacttggc     360
tgtgttgcca tccgcgtcac caaagcggag gaagtactgc cagccatcca aaaggctcga     420
gagatcaacg accgcccagt agtcatcgac ttcatcgtcg gtgaagacgc acaggtatgg     480
ccaatggtgt ctgctggatc atccaactcc gatatccagt acgcactcgg attgcgccca     540
ttctttgatg gtgatgaatc tgcagcagaa gatcctgccg acattcacga agccgtcagc     600
```

```
gacattgatg ccgccgttga atcgaccgag gcataaggag agacccaaga tggctaattc      660
tgacgtcacc cgccacatcc tgtccgtact cgttcaggac gtagacgatg acttttcccg      720
cgtatcaggt atgttcaccc gacgcgcatt caacctcgtg tccctcgtgt ctgcaaagac      780
cgaaacactc ggcatcaacc gcatcacggt tgttgtcgac gccgacgagc tcaacattga      840
gcagatcacc aagcagctca acaagctgat ccccgtgctc aaagtcgtgc gacttgatga      900
agagaccacc atcgcccgcg caatcatgct ggttaaggtc tctgcggata gcaccaaccg      960
tccgcagatc gtcgacgccg cgaacatctt ccgcgcccga gtcgtcgacg tggctccaga     1020
ctctgtggtt attgaatcca caggcacccc aggcaagctc cgcgcactgc ttgatgtgat     1080
ggaaccattc ggaatccgcg aactgatcca atccggacag attgcactca accgcggtcc     1140
gaagaccatg gctccggcca agatctaaac agcaattaat ctgattgcac ctgctgcata     1200
aatgtgacta gtcaaacacc gtctaattgc atgtgtgtgg tagaacaata atgtagttgt     1260
ctgcccaagc gagtttaact cccacgattt acagtggggg cagacatctt ttcaccaaaa     1320
tttttacgaa aggcgagatt ttctcccatg gctattgaac tgctttatga tgctgacgct     1380
gacctctcct tgatccaggg ccgcaaggtt gccataagct t                         1421

<210> SEQ ID NO 15
<211> LENGTH: 19
<212> TYPE: DNA
<213> ORGANISM: Corynebacterium glutamicum
<220> FEATURE:
<221> NAME/KEY: misc_feature
<222> LOCATION: (1)..(19)
<223> OTHER INFORMATION: test primer 3

<400> SEQUENCE: 15
cccagtagtc atcgacttc                                                    19

<210> SEQ ID NO 16
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: test primer 4

<400> SEQUENCE: 16
cagcgtcagc atcataaagc                                                   20
```

METHOD FOR PRODUCING L-LEUCINE, L-VALINE, L-ISOLEUCINE, α-KETOISOVALERATE, α-KETO-BETA-METHYLVALERATE, OR α-KETOISOCAPROATE USING RECOMBINANT CORYNEBACTERIA THAT CONTAIN THE ILVBN OPERON WHICH CAN BE INDUCED BY PROPIONATE

CROSS REFERENCE TO RELATED APPLICATIONS

The present application is U.S. national stage of international application PCT/EP2014/060680, which had an international filing date of May 23, 2014, and which was published in German under PCT Article 21(2) on Dec. 11, 2014. Priority is claimed to European application EP 13170248.2, filed on Jun. 3, 2013.

The invention relates to a process for the production of amino acids and keto acids using microorganisms, in which a promoter inducible by propionate makes possible the regulated expression of certain genes.

PRIOR ART

Amino acids and keto acids are used in human medicine, in the pharmaceutical industry, in cosmetics, in the foodstuffs industry and in animal nutrition.

Many of these compounds are produced by fermentation of strains of coryneform bacteria, in particular *Corynebacterium glutamicum*. Because of the great importance, work is constantly carried out on improving the production process. Process improvements can involve fermentation technology measures such as, for example, stirring and supply of oxygen, or the composition of the nutrient media such as, for example, the sugar concentration during the fermentation, or the working up to the product form by, for example, ion-exchange chromatography or the intrinsic performance characteristics of the microorganism itself.

For improving the performance characteristics of these microorganisms, methods of mutagenesis, selection and mutant selection are used. In this way, strains are obtained that are resistant to antimetabolites such as, for example, the valine analogue 2-thiazolealanine or the leucine analogue 4-azaleucine or 5,5,5-trifluoroleucine and that produce chemical compounds, for example the L-amino acids L-valine or L-leucine.

For some years, methods of recombinant DNA technique have likewise been employed for the strain improvement of L-amino acid-producing strains of *Corynebacterium glutamicum*, by, for example, amplifying or attenuating individual amino acid biosynthesis genes, for example, also with temporal regulation of the gene expression in the course of production, and investigating the effect on the production of the chemical compound.

Summarizing descriptions of the biology, genetics and biotechnology of *Corynebacterium glutamicum* are to be found in the "Handbook of *Corynebacterium glutamicum*" (Eds.: L. Eggeling and M. Bott, CRC Press, Taylor & Francis, 2005), in the special edition of the Journal of Biotechnology (Chief Editor: A. Pühler) with the title "A New Era in *Corynebacterium glutamicum* Biotechnology" (Journal of Biotechnology 104/1-3, (2003)) and in the book by T. Scheper (Managing Editor) "Microbial Production of L-Amino Acids" (Advances in Biochemical Engineering/Biotechnology 79, Springer Verlag, Berlin, Germany, 2003).

The nucleotide sequence of the genome of *Corynebacterium glutamicum* is described in Ikeda and Nakagawa (Applied Microbiology and Biotechnology 62, 99-109 (2003)), in EP 1 108 790 and in Kalinowski et al. (Journal of Biotechnology 104/1-3, (2003)).

The nucleotide sequences of the genome of *Corynebacterium glutamicum* are likewise available in the database of the National Center for Biotechnology Information (NCBI) of the National Library of Medicine (Bethesda, Md., USA), in the DNA Data Bank of Japan (DDBJ, Mishima, Japan) or in the nucleotide sequence database of the European Molecular Biologies Laboratories (EMBL, Heidelberg, Germany and Cambridge, UK).

Basically, there are two possibilities for the expression of genes. In continuous expression, the gene is continuously expressed by means of a constitutive promoter and the corresponding protein accumulates in the cell.

On the other hand, an inducible promoter is used in induced expression. The expression of the target gene is induced, that is enabled, by an inducer. This method is used if the (over) expression has negative effects on the production organism. Causes of this can be a high loading of the metabolic resources during the growth phase. The result is slower growth and thus prolonged runtimes of the bioreactor and associated therewith an increase in the costs in the case of industrial production. Induced expression is also advantageous in the case of cytotoxic products. Here, autointoxication and the death of the cell occurs after the induction of expression. With regard to the economy of a production process, it is therefore attempted to subdivide the process into a growth phase and a production phase. In the growth phase, an as large as possible amount of biomass is produced and in the production phase, the target protein is then produced by induction of the promoter. In this way, a maximal yield can be obtained, whereby the process becomes noticeably more economical.

For the regulatable *Escherichia coli* promoters lac, lambda PL and trp, it has already been shown that they can be employed in coryneform bacteria for the regulated expression of various genes (Tsuchiya and Morinaga, Bio/Technology 6 (1988) 428-431).

The ideal case for an inducible promoter is a coryneform promoter, which is regulated by a readily available, inexpensive substance.

EP 0530765 B1 (Kyowa Hakko) describes the use of an inducible promoter from Corynebacteria, here of the isocitrate lyase gene, for the production of enzymes such as [beta]-galactosidase, chloramphenicol acetyltransferase and ICL as well as physiologically active proteins, such as insulin or [alpha]-, [beta]- or [gamma]-interferon. This promoter leads to the expression of genes, as long as only a carbon source (C source) different from sugar is situated in the medium; in the presence of sugar it is repressed. As, however, sugars are employed as a C source in common fermentation media, it would be useful to obtain a regulatable promoter, which even in the presence of sugars leads to the expression of a gene using an inexpensive inducer.

DE 4440118 C1 (such as U.S. Pat. No. 5,965,391, F Z Jülich) claims the use of an inducible promoter from corynebacteria, here of the malate synthase gene aceB, for the production of proteins; inducers here are the carbon sources lactate, pyruvate or acetate.

The promoter of the prpDBC2 operon of *Corynebacterium glutamicum*, whose genes are essential as the main C source for growth on propionate, and code for the enzymes 2-methylcitrate dehydratase (PrpD2), 2-methylisocitrate lyase (PrpB2) and 2-methylcitrate synthase (PrpC2), was described by Plassmeier et al. (Journal of Biotechnology 159/1-2 (2012)). Analyses of promoter test vector constructs led to the identification of an operator region 121 base pairs long above the prpDBC2 operon, which is necessary for a propionate-induced transcription by the activator PrpR. EMSA studies showed that 2-methylcitrate probably functions as a coactivator of PrpR.

OBJECT OF THE INVENTION

The invention was based on the object of making available a novel process for the production of the L-amino acids L-leucine, L-valine or L-isoleucine, preferably L-valine, or of the α-keto acids α-ketoisovalerate, α-ketomethylvalerate or α-ketoisocaproate with a preferably improved yield and/or higher final concentration of the product intracellularly and/or in the medium. Here, an improvement in the specific yield (i.e. yield of desired product relative to carbon source employed) should preferably be present.

The novel process should preferably make it possible here to regulate the production of the L-amino acids and/or of the α-keto acids independently of the main carbon source of the medium.

In the novel process, the formation of undesired by-products, in particular the formation of the undesired by-product alanine, should moreover preferably be suppressed if possible, as the separation of the by-product is very laborious and costly and moreover has a negative effect on the product purity of the broth and the carbon yield.

The process employed should moreover preferably lead to an increase in the genetic stability of the strain employed for the production and thus make possible a high number of generations in the fermentation process (culturing stages and main fermenter) without a decrease in output data.

DESCRIPTION OF THE INVENTION

The object according to the invention is achieved by the use of an operator, to which the activator PrpR binds, for the regulation of the expression of the gene ilvBN.

ilvBN (EC No. 4.1.3.18) is the genes coding for the subunits of an acetolactate synthase.

The subject of the invention is therefore a process for the production of an L-amino acid selected from L-leucine, L-valine and L-isoleucine, preferably L-valine, or of an α-keto acid selected from ketoisovalerate, ketomethylvalerate and ketoisocaproate by fermentation of microorganisms of the genus *Corynebacterium*, containing in replicable form a polynucleotide with operator activity, the sequence of which is identical to at least 85%, preferably to at least 90, 92, 94 or 96%, in particular to at least 97, 98 or 99%, particularly preferably to 100%, to the sequence of position 1 to 121 according to SEQ ID NO: 1, 2 or 3, to which the activator PrpR binds and functionally downstream of which at the 3'-end are a second polynucleotide having promoter activity as well as the genes ilvB and ilvN coding for the subunits of an acetolactate synthase, and which regulates the transcription of the genes ilvBN as a function of the addition of the activator PrpR, which is activated by the co-activator 2-methylcitrate, in a medium to which, after a first phase without inducer, propionate or 2-methylcitrate is added in a subsequent second phase as an inducer, whereupon the ilvBN genes are expressed and thus the desired L-amino acid or α-keto acid is synthesized, under conditions in which the desired L-amino acid or α-keto acid is enriched in the medium or in the cells.

The polynucleotide having operator activity is preferably an operator which naturally regulates the expression of a 2-methylcitrate dehydratase in coryneform bacteria or a polynucleotide derived from such an operator.

The polynucleotide with operator activity preferably comprises a polynucleotide, the sequence of which is identical to at least 90%, preferably to at least 92, 94 or 96%, in particular to at least 97, 98 or 99%, particularly preferably to 100%, to the sequence according to SEQ ID NO: 11 or to the sequence from position 22 to position 49 according to SEQ ID NO: 1, 2 or 3 (in the following also called "IR 1") and also a polynucleotide, the sequence of which is identical to at least 90%, preferably to at least 92, 94 or 96%, in particular to at least 97, 98 or 99%, particularly preferably to 100%, to the sequence according to SEQ ID NO: 12 or to the sequence from position 77 to position 105 according to SEQ ID NO: 1, 2 or 3 (in the following also called "IR 2"). The sequence "IR 1" is arranged in position 22 to 49 here in a preferred embodiment in the polynucleotide with operator activity, while the sequence "IR 2" is arranged in position 77 to 105 in a preferred embodiment.

In a preferred embodiment according to the invention, the polynucleotide with operator activity is part of a longer polynucleotide, preferably of a polynucleotide having a sequence identity of at least 90%, preferably of at least 92, 94 or 96%, in particular of at least 97, 98 or 99%, particularly preferably of 100%, to the sequence of position 1 to 177 according to SEQ ID NO: 1, 2 or 3.

The gene ilvB is preferably a polynucleotide coding for a polypeptide having an amino acid sequence which has an identity of at least 90%, preferably of at least 92, 94 or 96%, in particular of at least 97, 98 or 99%, particularly preferably of 100%, to the amino acid sequence according to SEQ ID NO: 9.

Particularly preferably, it is here a polynucleotide, the sequence of which is identical to at least 90%, preferably to at least 92, 94 or 96%, in particular to at least 97, 98 or 99%, particularly preferably to 100%, to the sequence of position 499 to 2379 according to SEQ ID NO: 8.

The gene ilvN is preferably a polynucleotide coding for a polypeptide having an amino acid sequence which has an identity of at least 90%, preferably of at least 92, 94 or 96%, in particular of at least 97, 98 or 99%, particularly preferably of 100%, to the amino acid sequence according to SEQ ID NO: 10.

Particularly preferably, it is here a polynucleotide, the sequence of which is identical to at least 90%, preferably to at least 92, 94 or 96%, in particular to at least 97, 98 or 99%, particularly preferably to 100%, to the sequence of position 2393 to 2911 according to SEQ ID NO: 8.

The polypeptides encoded by the genes ilvB and ilvN agglomerate together to give a functional acetolactate synthase.

Propionate or propionic acid is preferably used for the induction of expression. In this respect, a "propionate induction" takes place. The propionate is converted in vitro to the actual co-activator, 2-methylcitrate. Alternatively, 2-methylcitrate can also be used directly for the induction, but is less preferably employed because of the lower availability. According to the invention, the term "propionate induction" also comprises the induction with 2-methylcitrate.

After completion of the production, the desired L-amino acid or α-keto acid is preferably isolated, other constituents of the fermentation broth and/or the biomass optionally remaining in their entirety or portions (>0 to 100%) in the isolated product or being completely removed.

In the process according to the invention, an induction-free culturing phase (growth phase, first phase) for the provision of biomass first takes place. In this phase, preferably no or hardly any amino acid or keto acid is formed (<5 g/l). In the subsequent production phase (induction phase, second phase), the production is induced by induction of the biosynthesis genes ilvBN by means of propionate or 2-methylcitrate. The culturing phase includes all culturing steps, starting from the retained sample, via preferably employed shaker flask stages up to the preferably employed culture fermenter. The culturing phase can also still comprise the first phase of the main fermentation. Preferably, the culturing phase is complete at the latest after the first 3-15 hours, preferably 5-10 hours, of the main fermentation.

The induction phase preferably comprises the time from 0-20 hours after inoculation of the main fermenter up to the end of the main fermentation. An induction at an earlier point in time, that is in the culture fermenter, can be advantageous and is a particular embodiment of the process according to the invention.

A precise regulation/metering of the propionic acid concentration in the production phase is necessary in order on the one hand to maintain the induction of the amino acid or keto acid synthesis and on the other hand to prevent the toxic action of the propionate or of one of its degradation intermediates (propionyl-CoA, 2-methyl-citrate). The preferred propionic acid concentration in the induction phase lies in the range from 0.1-10 g/l. The propionic acid can be added continuously in the form of a propionic acid feed or batchwise in the form of one or more propionic acid pulses at different times during the induction phase.

The single dose of the propionic acid as a media constituent of the main fermentation medium is likewise possible and is a particular embodiment of the process according to the invention.

A great problem in the production of amino acids and keto acids is normally the formation of by-products. The by-products formed decrease the carbon yield and must moreover optionally be separated off, which is very laborious and costly.

An example of the formation of a by-product is the formation of the by-product alanine in valine biosynthesis. The formation of alanine increases in the conventional production processes, in which a constitutive expression usually takes place, in dependence on the number of cell generations.

From the retention samples up to the harvesting of the production fermenter in a three-stage process (shaker flask, culture fermenter, main fermenter), approximately 20-25 generations are run through, in a four-stage process (shaker flask, PreSeed fermenter, culture fermenter, main fermenter) even over 30 generations are run through. In the running through of so many generations, the byproduct formation and biomass formation is normally correspondingly greatly increased.

According to the invention, however, a very strongly reduced by-product formation and biomass formation was found. Moreover, it was found that the by-product formation and biomass formation in production processes according to the invention is independent of the number of generations run through. This would suggest that the process management according to the invention leads to an increased genetic stability of the strain employed. The culturing phase can therefore in principle be extended to any length, which is particularly advantageous for the process management.

A particularly preferred process according to the invention is therefore distinguished in that it comprises at least four stages, namely at least three culturing stages and a production stage. Culturing here preferably comprises culturing in the shaker flask, in the PreSeed fermenter as well as in the seed fermenter. Production preferably takes place in a production fermenter.

A further particularly preferred process according to the invention is therefore distinguished in that the bacteria employed during the culturing phase run through at least 16, preferably at least 24, generations and/or during the entire fermentation (including culturing and production) run through at least 25, preferably at least 30, generations.

The invention also relates to the use of a polynucleotide having operator activity, to which the activator PrpR binds, the polynucleotide possessing a sequence which to at least 85%, 90%, 92%, 94%, 96%, 97%, 98%, 99% or 100%, preferably to at least 97%, particularly preferably to at least 98%, very particularly preferably to at least 99% and extremely preferably 100%, is identical to the sequence of position 1 to 121 according to SEQ ID NO: 1, 2 or 3, for the regulation of the expression of the genes ilvBN, preferably in combination with a promoter upstream of the genes.

The present invention also relates to an expression cassette, comprising a polynucleotide having operator activity, the sequence of which is identical to at least 85%, 90%, 92%, 94%, 96%, 97%, 98%, 99% or 100%, preferably to at least 97%, particularly preferably to at least 98%, very particularly preferably to at least 99% and extremely preferably 100%, to the sequence of position 1 to 121 according to SEQ ID NO:1, 2 or 3, a downstream promoter and the genes ilvBN coding for an acetolactate synthase.

The polynucleotide having operator activity here preferably always has the characteristics emphasized beforehand as preferred, in particular the conserved regions "IR 1" and "IR 2".

The promoter upstream of the ilvBN genes or the promoter downstream of the operator can be any desired promoter.

Examples of promoters according to the invention preferably employable in *Corynebacterium glutamicum* are described, for example, in FIG. 1 of the review article of Patek et al. (Journal of Biotechnology 104(1-3), 311-323 (2003)). In the same manner, the variants of the dapA promoter, for example the promoter A25, described by Vasicova et al (Journal of Bacteriology 181, 6188-6191 (1999)) can be employed. Furthermore, the gap promoter of *Corynebacterium glutamicum* (EP 06007373) can be used. Finally, the well-known promoters T3, T7, SP6, M13, lac, tac and trc described by Amann et al. (Genes 69(2), 301-315 (1988)) and Amann and Brosius (Genes 40(2-3), 183-190 (1985)) can be used.

In a preferred embodiment, the promoter employed according to the invention is a polynucleotide having promoter activity, the sequence of which is identical to at least 90%, 92%, 94%, 96%, 97%, 98%, 99% or 100%, preferably at least 97%, particularly preferably at least 98%, very particularly preferably at least 99% and extremely preferably 100%, to the sequence of position 122 to 206 according to SEQ ID NO: 4.

The expression cassette according to the invention is preferably an expression cassette having a sequence according to SEQ ID NO: 13.

A further subject of the present invention is a vector which contains an expression cassette according to the invention.

Kirchner and Tauch (Journal of Biotechnology 104:287-299 (2003)) describe a selection of the vectors preferably to be used in *Corynebacterium glutamicum*.

The homologous recombination using the vectors according to the invention allows the exchange of DNA sections on the chromosome for expression cassettes according to the invention, which are transported into the cell by the vector. For the efficient recombination between the annular DNA molecule of the vector and the target DNA on the chromosome, the DNA region to be exchanged, which contains an expression cassette according to the invention, is provided at the ends with nucleotide sequences homologous to the target site, whereby the site of the integration of the vector or of the exchange of the DNA is specified.

The incorporation of the expression cassette according to the invention can take place here at the native gene site of the ilvBN genes, preferably the native ilvBN genes and optionally also the native promoter of the ilvBN genes being replaced here by an expression cassette according to the invention.

Alternatively, an expression cassette according to the invention can also be integrated in an intergenic region in the chromosome, which has no encoding function, or at another gene site, the other gene site preferably being a nucleotide sequence on the chromosome, which is not essential for the growth of the cells and the production of the amino acid or keto acid.

The expression cassette according to the invention can also be incorporated according to the invention into the chromosome in a preferred embodiment in multiple copies and also optionally at different gene sites.

Instead of incorporating an expression cassette according to the invention into the chromosome, alternatively the operator used according to the invention can also be incorporated into the chromosome in combination with a promoter at the native gene site of the ilvBN genes, where preferably the native promoter of the ilvBN genes is replaced by the construct of operator and promoter.

Instead of incorporating the expression cassette according to the invention into the chromosome, according to the invention alternatively an extrachromosomally replicating vector can of course also be employed which contains an expression cassette according to the invention.

The present invention likewise further relates to a microorganism, preferably a *Corynebacterium*, especially a *Corynebacterium* that produces an L-amino acid selected from L-leucine, L-valine and L-isoleucine or an α-keto acid selected from ketoisovalerate, ketomethylvalerate and ketoisocaproate, which contains an expression cassette according to the invention and/or a vector according to the invention.

Details of the biochemistry and chemical structure of polynucleotides, such as they occur in living beings, such as, for example, microorganisms, are found, inter alia, in the textbook "Biochemie" [Biochemistry] of Berg et al (Spektrum Akademischer Verlag Heidelberg.Berlin, Germany, 2003; ISBN 3-8274-1303-6).

If the polynucleotide consists of deoxyribonucleotide monomers containing the nucleobases or bases adenine (A), guanine (G), cytosine (C) and thymine (T), deoxyribopolynucleotides or deoxyribonucleic acid (DNA) are spoken of. If the polynucleotide consists of ribonucleotide monomers containing the nucleobases or bases adenine (A), guanine (G), cytosine (C) and uracil (U), ribo-polynucleotides or ribonucleic acid (RNA) are spoken of. In the polynucleotides mentioned, the monomers are connected covalently to one another by a 3'-5'-phosphodiester bond.

A "polynucleotide with operator activity" or an "operator" is understood as meaning a polynucleotide, preferably deoxyribopolynucleotide, or a nucleic acid, preferably deoxyribonucleic acid (DNA), which functionally linked by means of a polynucleotide with promoter activity to a polynucleotide to be transcribed switches on or switches off the transcription of this polynucleotide by interaction with various regulatory proteins (activators or repressors, which in turn interact with ligands or effector molecules).

A "polynucleotide with promoter activity" or a "promoter" is understood as meaning a polynucleotide, preferably deoxyribopolynucleotide, or a nucleic acid, preferably desoxyribonucleic acid (DNA), which functionally linked to a polynucleotide to be transcribed specifies the initiation point and the initiation frequency of the transcription of this polynucleotide, whereby the level of expression of the controlled polynucleotide can be influenced.

On account of the double-stranded structure of DNA, the invention likewise relates to the strand complementary to the strand of the sequence listing in SEQ ID NO: 1, 2 or 3.

"Transcription" is understood as meaning the process by which, starting from a DNA matrix, a complementary RNA molecule is produced. Proteins, such as RNA polymerase, "Sigma factors" and transcriptional regulator proteins are involved in this process. The RNA synthesized (messenger RNA, m-RNA) then serves as a matrix in the process of translation, which then leads to the polypeptide or protein.

A gene, seen from a chemical point of view, is a polynucleotide. A polynucleotide that encodes a protein/polypeptide is used here synonymously to the term "gene". Accordingly, the two terms "gene" and "coding region" are used synonymously and likewise the two terms "protein" and "polypeptide".

A "functional downstream connection or linkage" is understood in this connection as meaning the sequential arrangement of the polynucleotide having operator activity according to the invention with a second polynucleotide having promoter activity and with a further oligo- or polynucleotide that leads to a transcription of the further polynucleotide.

If the further polynucleotide is a polynucleotide that codes for a polypeptide/protein consisting of the coding region for a polypeptide beginning with a start codon, inclusive of the stop codon and optionally inclusive of a transcription terminator, "functional downstream connection or linkage" means the sequential arrangement that leads to a transcription of the further polynucleotide and the translation of the synthesized RNA.

The further polynucleotide codes for one or more polypeptide(s). A polynucleotide coding for a protein/polypeptide consists essentially of a start codon, selected from the group consisting of ATG, GTG and TTG, preferably ATG or GTG, particularly preferably ATG, of a protein-encoding sequence and one or more stop codon(s) selected from the group consisting of TAA, TAG and TGA.

If the further polynucleotide codes for a number of proteins/polypeptides, a ribosome binding site can be situated before each gene. After the last gene is optionally situated a terminator.

The further polynucleotide consists according to the invention of the genes ilvB and ilvN, which code for the subunits of an acetolactate synthase (IlvBN, EC No.: 4.1.3.18).

The invention furthermore relates to the use of the expression cassette according to the invention or of the vector according to the invention for the expression of the ilvBN genes in microorganisms. The expression cassette according to the invention guarantees the transcription and the translation of the synthesized RNA, preferably mRNA, to polypeptides, namely of the two subunits of an acetolactate synthase.

Using the expression cassette according to the invention, the genes ilvBN in microorganisms can be expressed or overexpressed at a desired time.

Overexpression is generally understood as meaning an increase in the intracellular concentration or activity of a ribonucleic acid, of a protein (polypeptide) or of an enzyme in comparison to the starting strain (parent strain) or wild-type strain, if this is the starting strain. A starting strain (parent strain) is understood as meaning the strain on which the measure leading to the overexpression was carried out.

In the case of overexpression the methods of recombinant overexpression are preferred. Among these are grouped all methods in which a microorganism is produced using a DNA molecule prepared in-vitro. Such DNA molecules comprise, for example, promoters, expression cassettes, genes, alleles, coding regions etc. These are converted by methods of transformation, conjugation, transduction or similar methods to the desired microorganism.

By means of the measures of overexpression using the operator to be employed according to the invention and/or using the expression cassette according to the invention, the activity or concentration of the acetolactate synthase is in general preferably increased by at least 10%, 25%, 50%, 75%, 100%, 150%, 200%, 300%, 400% or 500%, preferably maximally to 1000%, 2000%, 4000%, 10000% or 20000%, based on the activity or concentration of the polypeptide in the strain before the measure leading to the overexpression.

The extent of the expression or overexpression can be determined by measurement of the amount of mRNA transcribed by the gene, by determination of the amount of the polypeptide and by determination of the enzyme activity.

For the determination of the amount of mRNA, inter alia the method of "Northern Blotting" and quantitative RT-PCR can be used. In the quantitative RT-PCR, the polymerase chain reaction is preceded by a reverse transcription. For this purpose, the LightCycler™ System of the company Roche Diagnostics (Boehringer Mannheim GmbH, Roche Molecular Biochemicals, Mannheim, Germany) can be used, as described, for example in Jungwirth et al. (FEMS Microbiology Letters 281, 190-197 (2008)). The concentration of the protein in the gel can be determined by means of 1- and 2-dimensional protein gel separation and subsequent optical identification of the protein concentration using appropriate analysis software. A conventional method for the preparation of the protein gels in the case of coryneform bacteria and for the identification of the proteins is the procedure described by Hermann et al. (Electrophoresis, 22:1712-23 (2001)). The protein concentration can likewise be determined by Western Blot hybridization using an antibody specific for the protein to be detected (Sambrook et al., Molecular cloning: a laboratory manual. $2^{nd}$ Ed. Cold Spring Harbor Laboratory Press, Cold Spring Harbor, N. Y., 1989) and subsequent optical assessment using appropriate software for the concentration determination (Lohaus and Meyer (1998) Biospektrum 5:32-39; Lottspeich, Angewandte Chemie 321: 2630-2647 (1999)). The statistical significance of the data gathered is determined by means of a T test (Gosset, Biometrika 6(1): 1-25 (1908)).

The measure for the overexpression of the ilvBN genes using the operator to be employed according to the invention can be combined in a suitable manner with further measures for the overexpression.

For the achievement of an overexpression, a multiplicity of methods are available in the prior art. These also include, in addition to the modification of the nucleotide sequences that govern or control the expression of the gene, the increase in the copy number.

The increase in the copy number can take place by means of plasmids, which replicate in the cytoplasm of the microorganism. For this purpose, in the prior art a plethora of plasmids are described for the variety of groups of microorganisms with which the desired increase in the copy number of the gene can be adjusted. Suitable plasmids for the genus Corynebacterium are described, for example, in Tauch et al. (Journal of Biotechnology 104 (1-3), 27-40, (2003)), or in Stansen et al. (Applied and Environmental Microbiology 71, 5920-5928 (2005)).

The increase in the copy number by at least one (1) copy can furthermore take place by insertion of further copies into the chromosome of the microorganism. Suitable methods for the genus Corynebacterium are described, for example, in the patent specifications WO 03/014330, WO 03/040373 and WO 04/069996.

The increase in the gene expression can furthermore take place in that a number of promoters are positioned before the desired gene or functionally linked to the gene to be expressed and in this way increased expression is achieved. Examples of this are described in the patent specification WO 2006/069711.

The rate of elongation is influenced by the codon usage; by the use of codons for t(transfer) RNAs frequently occurring in the starting strain the translation can be increased. In addition, the exchange of a start codon for the codon ATG occurring most frequently in many microorganisms (77% in Escherichia coli) can considerably improve the translation, as at the RNA level the codon AUG is two to three times more effective than, for example, the codons GUG and UUG (Khudyakov et al., FEBS Letters 232(2):369-71 (1988); Reddy et al., Proceedings of the National Academy of Sciences of the USA 82(17):5656-60 (1985)). The sequence environment of the start codon can also be optimized, as interacting effects between the start codon and the flanking regions are described (Stenstrom et al., Gene 273(2):259-65 (2001); Hui et al., EMBO Journal 3(3):623-9 (1984)).

Instructions for handling of DNA, digestion and ligation of DNA, transformation and selection of transformants is found, inter alia, in the known Handbook of Sambrook et al. Molecular Cloning: A Laboratory Manual, Second Edition (Cold Spring Harbor Laboratory Press, 1989).

In a preferred embodiment according to the invention, microorganisms are employed in which further genes of the biosynthetic pathway of the desired L-amino acid or α-keto acid are additionally present in amplified form, in particular overexpressed.

In connection with the production of L-valine, L-isoleucine, α-ketoisovaleric acid, α-keto-β-methylvaleric acid or α-ketoisocaproic acid, preferably one or more of the genes or polynucleotides which code for enzymes of the biosynthesis of L-valine, L-isoleucine, α-ketoisovaleric acid, α-keto-β-methylvaleric acid or α-ketoisocaproic acid, selected from the group:
a) polynucleotide (ilvC gene), which codes for an isomeroreductase (IlvC, EC No.: 1.1.1.86),
b) polynucleotide (ilvD gene), which codes for a dihydroxy acid dehydratase (IlvD, EC No.: 4.2.1.9),
c) polynucleotide (ilvE gene), which codes for a transaminase (IlvE, EC No.: 2.6.1.42),
d) polynucleotide (ilvA gene), which codes for a threonine dehydratase (IlvA, EC No.: 4.3.1.19),
e) polynucleotide (hom gene), which codes for a homoserine dehydrogenase (Hom, EC No.: 1.2.1.11)
f) polynucleotide (thrB gene), which codes for a homoserine kinase (ThrB, EC No.: 2.7.1.39)

g) polynucleotide (thrC gene), which codes for a threonine synthase (ThrC, EC No.: 4.2.3.1)
h) polynucleotide (leuA gene), which codes for an isopropylmalate synthase (LeuA, EC No.: 2.3.3.13)
i) polynucleotide (leuB gene), which codes for an isopropylmalate dehydrogenase (LeuB, EC No.: 1.1.1.85)
j) polynucleotide (leuC gene), which codes for the large subunit of an isopropylmalate isomerase (LeuC, EC No.: 4.2.1.33)
k) polynucleotide (leuD gene), which codes for the small subunit of an isopropylmalate isomerase (LeuD, EC No.: 4.2.1.33) can additionally be overexpressed, the genes hom, ilvA, ilvC, ilvD and ilvE being particularly preferred for isoleucine and valine, the genes ilvC and ilvD being particularly preferred for α-ketoisovaleric acid (KIV) and α-keto-β-methylvaleric acid (KMV) and the genes ilvC, ilvD, leuA, leuB, leuC and leuD being particularly preferred for α-ketoisocaproic acid (KIC).

In a preferred embodiment, microorganisms are employed in which the metabolic pathways which reduce the formation of the desired L-amino acid or α-keto acid are at least partially attenuated.

If the production of valine or ketoisovalerate is preferred, then the metabolic pathways for isoleucine (for the formation of the precursor alpha-ketobutyric acid: ilvA, thrB, thrC, hom) and/or for leucine (leuA, leuB, leuCD) can be attenuated. If the production of isoleucine or ketomethyl valerate is preferred, then the biosynthetic pathway of leucine can be attenuated. If the production of leucine or ketoisocaproate is preferred, then the biosynthetic pathway of isoleucine (or the precursor alpha-ketobutyric acid) can be attenuated.

The term "attenuation" in this connection describes the reduction or switching off of the intracellular activity of one or more enzymes (proteins) in a bacterium, which are encoded by the appropriate DNA, by, for example, using a weak promoter or using a gene or allele that codes for an appropriate enzyme having a low activity or inactivates the appropriate gene or enzyme (protein) and optionally combines these measures. The complete or the partial attenuation of individual target genes can be achieved, e.g., by complete or partial deletion of the genes or by insertion of point mutations in the structural gene or in the promoter region or in the ribosome binding site. A further method for the specific reduction of the gene expression is the antisense technique, where short oligodeoxynucleotides or vectors for the synthesis of longer antisense RNA are brought into the target cells. The antisense RNA can bind there to complementary sections of specific mRNAs and reduce their stability or block the translatability. The person skilled in the art finds an example of this in Srivastava et al. (Applied Environmental Microbiology 2000 October; 66 (10): 4366-4371). The antisense technique just described can also be carried out by use of the operators/promoter according to the invention, in which this is cloned in "anti-sense" orientation behind the target gene. After addition of the inducer propionate, the formation of an mRNA of the complementary strand of the target gene to be attenuated is induced. By addition of this anti-sense mRNA to the mRNA of the target gene, the expression of the target gene is reduced. The regulated expression or overexpression of the genes ilvBN or production of the L-amino acids or α-keto acids is preferably carried out in microorganisms of the genus *Corynebacterium*. Within the genus *Corynebacterium*, the preferred strains are those that are based on the following species: *Corynebacterium efficiens*, the type strain being deposited as DSM44549, *Corynebacterium glutamicum*, the type strain being deposited as ATCC13032, and *Corynebacterium ammoniagenes*, the type strain being deposited as ATCC6871. The species *Corynebacterium glutamicum* is very particularly preferred.

Some representatives of the species *Corynebacterium glutamicum* are also known in the prior art under other names. These include, for example: strain ATCC13870, which was designated as *Corynebacterium acetoacidophilum*, strain DSM20137, which was designated as *Corynebacterium lilium*, strain ATCC17965, which was designated as *Corynebacterium melassecola*, strain ATCC14067, which was designated as *Brevibacterium flavum*, strain ATCC13869, which was designated as *Brevibacterium lactofermentum*, and strain ATCC14020, which was designated as *Brevibacterium divaricatum*.

The term "*Micrococcus* glutamicus" for *Corynebacterium glutamicum* was likewise common. Some representatives of the species *Corynebacterium efficiens* were also designated in the prior art as *Corynebacterium thermoaminogenes*, such as, for example, the strain FERM BP-1539.

The microorganisms or strains (starting strains) employed for the measures according to the invention preferably already have the ability to secrete the desired L-amino acid or α-keto acid into the nutrient medium surrounding them and to accumulate it there. In the following, the expression "produce" is also used for this. In particular, the strains employed according to the invention preferably have the ability after induction to enrich or to accumulate (at least) 0.5 g/l*h, preferably at least 1.0 or 2.0 g/l*h, of the desired amino acid or keto acid in the cell or in the nutrient medium. The starting strains are preferably strains that have been produced by mutagenesis and selection, by recombinant DNA techniques or by a combination of both methods.

It is comprehensible for the person skilled in the art that it is also possible to arrive at a microorganism suitable for the measures of the invention by firstly employing, in a wild strain, such as, for example, in the *Corynebacterium glutamicum* type strain ATCC 13032 or in the strain ATCC 14067, an operator to be used according to the invention for the regulated expression of the desired genes and subsequently by inducing the microorganism to produce the amino acid or keto acid by further genetic measures described in the prior art.

Known representatives of strains of coryneform bacteria producing or secreting L-valine are, for example: *Brevibacterium lactofermentum* FERM BP-1763 (described in U.S. Pat. No. 5,188,948); *Brevibacterium lactofermentum* FERM BP-3007 (described in U.S. Pat. No. 5,521,074); *Corynebacterium glutamicum* FERM BP-3006 (described in U.S. Pat. No. 5,521,074); and *Corynebacterium glutamicum* FERM BP-1764 (described in U.S. Pat. No. 5,188,948).

Microorganisms producing L-valine typically have a feedback-resistant or desensitized acetolactate synthase (AHAS, EC 4.1.3.18). It represents the first enzyme of the parallel metabolic pathways for the synthesis of isoleucine, valine and leucine (Umbarger, H. E. 1987, Biosynthesis of the branched-chain amino acids, pp. 352-367, in F. C. Neidhardt, J. L. Ingraham, K. B. Low, B. Magasanik, M. Schaechter, and H. E. Umbarger (ed.), *Escherichia coli* and *Salmonella typhimurium*: Cellular and Molecular Biology, American Society for Microbiology, Washington, D.C.). The holoenzyme always consists of 2 large subunits and 2 small subunits. The large AHAS subunit forms the catalytic domain and is encoded by ilvB; the small subunit, which functions as a regulatory domain, is encoded by ilvN. Feedback-resistant acetolactate synthases are understood as meaning acetolactate synthases, which in comparison to the wild form (wild-type) have a lower sensitivity to inhibition by the branched-chain amino acids valine, leucine and isoleucine or mixtures of these. In the case of the acetolactate synthases of the species *Corynebacterium glutamicum*, the strains ATCC13032, ATCC14067 (also known as *Brevibacterium flavum*) or ATCC13869 (also known as *Brevibacterium lactofermentum*) are the suitable wild-type.

The genes ilvBN in *Corynebacterium glutamicum* coding for acetolactate synthase are described, for example, by Keilhauer et al. (Journal of Bacteriology 175(17):5595-603 (1993)) or in EP1108790. The accession number L09232 (GenBank, NCBI) shows the sequence of the genes.

Enzyme variants of AHAS, which are no longer subject to the feedback inhibition by the branched-chain amino acids (leucine, valine, isoleucine), are described, for example, in Mendel et al. (Journal of Molecular Biology 325, 275-284 (2003)), Elisakova et al. (Applied and Environmental Microbiology 71, 207-213 (2005)), Wada et al. (Bioscience Biotechnology & Biochemistry, 72 (11), 2959-2965, (2008)) and in EP1491634. Variants of a feedback-resistant acetolactate synthase are preferred which carry one or more of the following amino acid replacements in the small subunit encoded by ilvN, selected from the group: in position 20 of the amino acid sequence L-aspartic acid instead of glycine, in position 21 of the amino acid sequence L-aspartic acid instead of L-isoleucine, in position 22 of the amino acid sequence L-phenylalanine instead of L-isoleucine, in position 42 of each proteinogenic amino acid excepting L-alanine, preferably L-valine, L-isoleucine and L-leucine, particularly preferably L-valine and optionally in position 47 L-leucine instead of L-histidine (described in DE 102011118019 A1).

Known representatives of L-isoleucine-producing or secreting strains of coryneform bacteria are, for example: *Brevibacterium flavum* FERM BP-760 (described in U.S. Pat. No. 4,656,135); *Brevibacterium flavum* FERM BP-2215 (described in U.S. Pat. No. 5,294,547); and *Corynebacterium glutamicum* FERM BP-758 (described in U.S. Pat. No. 4,656,135).

α-Keto acid-secreting or -producing strains are based, for example, on: *Corynebacterium glutamicum*, strain ATCC13032; *Brevibacterium flavum*, strain ATCC 14067; and *Brevibacterium lactofermentum*, strain ATCC 13869.

The present invention provides a microorganism which produces an L-amino acid selected from L-leucine, L-valine and L-isoleucine or an α-keto acid selected from α-ketoisovalerate, α-ketomethylvalerate and α-ketoisocaproate, the microorganism making possible or having by the use of the operator to be employed according to the invention a regulated expression of the genes ilvBN coding for acetolactate synthase.

Furthermore, the present invention makes available a process for the fermentative production of an L-amino acid selected from L-leucine, L-valine and L-isoleucine or of an α-keto acid selected from α-ketoisovalerate, α-ketomethylvalerate and α-ketoisocaproate comprising the steps:
a) culturing of a microorganism according to the invention in a suitable medium, a fermentation broth being obtained, and
b) enriching of the L-amino acid or the α-keto acid in the fermentation broth from a) and/or in the cells of the microorganism.

It is preferred here that the L-amino acid or α-keto acid or a liquid or solid product that contains the L-amino acid or α-keto acid is obtained from the fermentation broth containing the L-amino acid or the α-keto acid.

The microorganisms produced can be cultured continuously—as described, for example, in WO 05/021772—or batchwise in the batch process (batch culturing or batch process) or in the fed batch (feed process) or repeated fed batch process (repetitive feed process) for the purpose of production of the desired organic chemical compound. A general summary of known culturing methods is available in the textbook of Chmiel (Bioprozesstechnik 1, Einführung in die Bioverfahrenstechnik [Bioprocess Technology 1, Introduction to Bioprocess Technology] (Gustav Fischer Verlag, Stuttgart, 1991)) or in the textbook of Storhas (Bioreaktoren and periphere Einrichtungen [Bioreactors and Peripheral Devices] (Vieweg Verlag, Braunschweig/Wiesbaden, 1994)).

The culture medium or fermentation medium to be used must satisfy the demands of the respective strains in a suitable manner. Descriptions of culture media for various microorganisms are contained in the handbook "Manual of Methods for General Bacteriology" of the American Society for Bacteriology (Washington D.C., USA, 1981). The terms culture medium and fermentation medium or medium are mutually interchangeable.

The carbon source used can be sugars and carbohydrates such as, e.g., glucose, sucrose, lactose, fructose, maltose, molasses, sucrose-containing solutions from sugar beet or sugar cane processing, starch, starch hydrolysate and cellulose, oils and fats, such as, for example, soya bean oil, sunflower oil, peanut oil and coconut oil, fatty acids, such as, for example, palmitic acid, stearic acid and linoleic acid, alcohols, such as, for example, glycerol, methanol and ethanol and organic acids, such as, for example, acetic acid or lactic acid.

The nitrogen source used can be organic nitrogen-containing compounds such as peptones, yeast extract, meat extract, malt extract, corn steep liquor, soya bean meal and urea or inorganic compounds such as ammonium sulphate, ammonium chloride, ammonium phosphate, ammonium carbonate and ammonium nitrate. The nitrogen sources can be used individually or as a mixture.

The phosphorus source used can be phosphoric acid, ammonium phosphate, potassium dihydrogenphosphate or dipotassium hydrogenphosphate or the corresponding sodium-containing salts.

The culture medium must furthermore contain salts, for example, in the form of chlorides or sulphates of metals such as, for example, sodium, potassium, magnesium, calcium and iron, such as, for example, magnesium sulphate or iron sulphate, which are necessary for growth. Finally, essential growth substances, such as amino acids, for example, homoserine and vitamins, for example thiamine, biotin or pantothenic acid can be employed additionally to the above-mentioned substances.

Propionate is preferably added to the medium as a salt, but can also be added as propionic acid. Suitable salts of propionic acid are magnesium propionate, sodium propionate, calcium propionate, ammonium propionate and potassium propionate. Propionate is present in the medium dissolved as the free acid or as the propionate anion.

The feedstocks mentioned can be added to the culture in the form of a single batch or in a suitable manner during culturing.

For the control of the pH of the culture, basic compounds such as sodium hydroxide, potassium hydroxide, ammonia, ammonium hydroxide or ammonia water or acidic compounds such as phosphoric acid or sulphuric acid are suitably employed. The pH is in general adjusted to a value of 6.0 to 8.5, preferably 6.5 to 8. For the control of foam development, anti-foam agents, such as, for example, fatty acid polyglycol esters, can be employed. For the maintenance of the stability of plasmids, suitable selectively acting substances, such as, for example, antibiotics, can be added to the medium. The fermentation is preferably carried out under aerobic conditions. In order to maintain these, oxygen or oxygen-containing gas mixtures, such as, for example, air, are added to the culture. The use of liquids that are enriched with hydrogen peroxide is likewise possible. Fermentation under oxygen-limiting conditions is a further particular embodiment according to the invention. Optionally, the fermentation is run at overpressure, for example at an overpressure of 0.03 to 0.2 MPa. The temperature of the culture is normally 20° C. to 45° C. and preferably 25° C. to 40° C., particularly preferably 30° to 37° C. In batch- or fed-batch processes the culturing is preferably continued until an amount sufficient for the measure of the recovery of the desired organic chemical compound has formed. This target is normally achieved within 10 hours to 160 hours. In continuous processes, longer culturing times are possible. Owing to the activity of the microorganisms, an enrichment (accumulation) of the organic chemical compound in the fermentation medium and/or in the cells of the microorganisms occurs.

Examples of suitable fermentation media are found, inter alia, in the patent specifications U.S. Pat. Nos. 5,770,409, 5,990,350, 5,275,940, WO 2007/012078, U.S. Pat. No. 5,827,698, WO 2009/043803, U.S. Pat. Nos. 5,756,345 or 7,138,266.

The analysis of L-amino acids for the determination of the concentration at one or more time(s) in the course of the fermentation can be carried out by separation of the L-amino acids by means of ion-exchange chromatography, preferably cation-exchange chromatography with subsequent post-column derivatization using ninhydrin, such as described in Spackman et al. (Analytical Chemistry 30: 1190-1206 (1958)). Instead of ninhydrin, ortho-phthaldialdehyde can also be employed for the post-column derivatization. A review article on ion-exchange chromatography is found in Pickering (LC.GC (Magazine of Chromatographic Science) 7(6), 484-487 (1989)).

It is likewise possible to perform a pre-column derivatization, for example, using ortho-phthaldialdehyde or phenyl isothiocyanate and to separate the resulting amino acid derivatives by reversed-phase chromatography (RPC), preferably in form of high-performance liquid chromatography (HPLC). Such a method is described, for example, in Lindroth et al. (Analytical Chemistry 51: 1167-1174 (1979)).

Detection is carried out photometrically (absorption, fluorescence).

A comprehensive presentation on amino acid analysis is found, inter alia, in the textbook "Bioanalytik" of Lottspeich and Zorbas (Spektrum Akademischer Verlag, Heidelberg, Germany 1998).

The analysis of α-keto acids for the determination of the concentration at one or more time(s) in the course of the fermentation can be carried out by separation of the keto acids and other excretion products by means of ion-exchange chromatography, preferably cation-exchange chromatography on a sulphonated styrene/divinylbenzene polymer in the H$^+$form, e.g. by means of 0.025 N sulphuric acid with subsequent UV detection at 215 nm (alternatively also at 230 or 275 nm). Preferably, a REZEX RFQ—Fast Fruit H+ column (Phenomenex) can be employed; other suppliers for the separation phase (e.g. Aminex of BioRad) are possible. Analogous separations are described in appropriate application examples of the supplier.

The analysis of propionic acid for the determination of the concentration at one or more time(s) in the course of the fermentation can by achieved by separation of the organic acids by means of HPLC. A VARIAN MetaCarb H+300×7.8 mm A5215 (300 mm long, 7.8 mm diameter) was used as the column. A mixture of sulphuric acid and acetonitrile (215 ml of 0.5M sulphuric acid, 50 ml of acetonitrile, to 5 l with distilled water) served as the eluent. 0.005 M sulphuric acid served as the solvent for the running samples. The cell-free running samples were diluted 1:20 here.

The separation parameters were as follows: flow rate 0.4 ml/min; injection volume of the sample 20 µl; temperature 35° C. Detection takes place photometrically at 215 nm by UV. The retention time of the propionic acid was 30.258 min. The measurable range was between 0.09 and 7.514 g/l.

The performance of the processes or fermentation processes according to the invention with respect to one or more of the parameters selected from the group consisting of the concentration (compound formed per volume), the yield (compound formed per carbon source consumed), the formation (compound formed per volume and time) and the specific formation (compound formed per cell dry mass or bio dry mass and time or compound formed per cell protein and time) or also other process parameters and combinations thereof, is preferably increased according to the invention by at least 0.5%, at least 1%, at least 1.5% or at least 2% in comparison to processes or fermentation processes using microorganisms, in which the expression cassette according to the invention is not present. This is to be regarded as very valuable in the context of a large-scale process.

By means of the measures of the fermentation, a fermentation broth is obtained which contains the desired amino acid or keto acid.

Subsequently, the provision or production or extraction of a product containing the amino acid or keto acid in liquid or solid form takes place.

A fermentation broth is understood as meaning a fermentation medium or nutrient medium, in which a microorganism has been cultured for a certain time and at a certain temperature. The fermentation medium or the media employed during the fermentation contains/contain all substances or components, which ensure production of the desired compound and typically the replication or viability.

On conclusion of the fermentation, the resulting fermentation broth accordingly contains a) the biomass (cell mass) of the microorganism formed as a result of the replication of the cells of the microorganism, b) the desired amino acid or keto acid formed in the course of the fermentation, c) the organic by-products optionally formed in the course of the fermentation, and d) the constituents of the fermentation medium employed or the feedstocks such as, for example, vitamins, such as biotin or salts such as magnesium sulphate not consumed by the fermentation.

The organic by-products include substances that are produced by the microorganisms employed in the fermentation in addition to the respective desired compound and are optionally excreted.

The fermentation broth is removed from the culture vessel or the fermentation container, optionally collected, and used to prepare a product containing the amino acid or keto acid in liquid or solid form. For this, the expression "obtainment of the fine chemical-containing product" is also used. In the simplest case, the fine chemical-containing fermentation broth removed from the fermentation container is itself the product obtained.

By means of one or more of the measures selected from the group consisting of
a) partial (>0% to <80%) to complete (100%) or almost complete (≥80%, ≥90%, ≥95%, ≥96%, ≥97%, ≥98%, ≥99%) removal of the water,
b) partial (>0% to <80%) to complete (100%) or almost complete (≥80%, ≥90%, ≥95%, ≥96%, ≥97%, ≥98%, ≥99%) removal of the biomass, this optionally being inactivated before the removal,
c) partial (>0% to <80%) to complete (100%) or almost complete (≥80%, ≥90%, ≥95%, ≥96%, ≥97%, ≥98%, ≥99%, ≥99.3%, ≥99.7%) removal of the organic byproducts formed in the course of the fermentation, and
d) partial (>0%) to complete (100%) or almost complete (≥80%, ≥90%, ≥95%, ≥96%, ≥97%, ≥98%, ≥99%, ≥99.3%, ≥99.7%) removal of the constituents of the fermentation medium employed or of the feedstocks which constituents have not been consumed by the fermentation,
a concentration or purification of the desired organic chemical compound is achieved from the fermentation broth. In this manner, products are isolated that have a desired content of the compound.

The partial (>0% to <80%) to complete (100%) or almost complete (≥80% to <100%) removal of the water (measure a)) is also designated as drying.

In one variant of the process, pure (≥80% by wt., ≥90% by wt.) or highly pure (≥95% by wt., ≥97% by wt., ≥99% by wt.) product forms of the desired organic chemical compound, preferably L-amino acids, are accessed by complete or almost complete removal of the water, of the biomass, of the organic by-products and of the unconsumed constituents of the fermentation medium employed. For the measures according to a), b), c) or d), a plethora of technical instructions are available in the prior art.

In the case of processes for the production of L-amino acids L-leucine, L-valine or L-isoleucine or the α-keto acids ketoisovalerate, ketomethylvalerate or ketoisocaproate using bacteria of the genus *Corynebacterium*, those processes are preferred in which products are obtained that contain no constituents of the fermentation broth. These are used in particular in human medicine, in the pharmaceutical industry and in the foodstuffs industry.

The process according to the invention serves for the fermentative production of the L-amino acids L-leucine, L-valine or L-isoleucine or of the α-keto acids ketoisovalerate, ketomethylvalerate or ketoisocaproate.

The invention finally relates to the use of the microorganism according to the invention for the fermentative production of the L-amino acids L-leucine, L-valine or L-isoleucine or of the α-keto acids ketoisovalerate, ketomethylvalerate or ketoisocaproate.

The present invention is explained in more detail below with the aid of exemplary embodiments.

EXAMPLE 1

Cloning of the Replacement Construct μL18mobsacB_PprpD2-ilvB

Starting from the genome sequence of *Corynebacterium glutamicum* ATCC14067, at the company Life Technologies GmbH (Darmstadt, Germany) a DNA fragment 1390 by in size was synthesized (Seq ID NO: 5) which consists of the following components:
homologous DNA region upstream of ilvB
PprpD2 promoter from *C. glutamicum* ATCC14067
ribosome binding site of the gap gene from *C. glutamicum* ATCC14067
homologous region to the ilvB gene, which instead of the GTG start codon carries an ATG start codon.

The fragment was cloned by means of the terminally introduced cleavage sites EcoRI and HindIII by respective cleavage using the two restriction enzymes mentioned and subsequent ligation in the vector pK18mobsacB analogously cleaved using EcoRI and HindIII. The plasmid bears the designation pK18mobsacB_PprpD2-ilvB. It allows the production of a mutant in which the native promoter of the ilvB gene is deleted and replaced by the inducible promoter PprpD2. In this, the native start codon (GTG) is moreover replaced by the start codon ATG preferred by the ribosome.

EXAMPLE 2

Construction of the Replacement Construct pK18mobsacB_ilvN(M13)

Starting from the genome sequence of *Corynebacterium glutamicum* ATCC14067, at the company Life Technologies GmbH (Darmstadt, Germany) a DNA fragment 1421 bp in size was synthesized (Seq ID NO: 14), which comprises a part of the ilvB gene, the intergene region between ilvB gene and ilvN gene, and also a part of the ilvN gene. In this, the native sequence "GGAATCATT" in the ilvN gene (+58 to +66 bp downstream of the gene start of ilvN, the gene start being defined as +1), was changed to "GATGACTTT". Thereby, the amino acid sequence of the IlvN protein at the positions 20, 21 and 22 is changed from Gly (20), Ile(21), Ile(22) to Asp (20), Asp (21), Phe(22).

The fragment was ligated by means of the terminally introduced cleavage sites EcoRI and HindIII by respective cleavage using the two restriction enzymes mentioned and subsequent ligation in the vector pK18mobsacB analogously cleaved using EcoRI and HindIII. The plasmid bears the designation pK18mobsacB_ilvN(M13). It allows the production of a mutant, in which the native gene sequence "GGAATCATT" (+58 to +66 bp downstream of the gene start of ilvN, the gene start being defined as +1) is changed to "GATGACTTT".

EXAMPLE 3

Construction of the Mutants *C. glutamicum* ATCC14067_PprpD2-ilvBN, *C. glutamicum* ATCC14067_ilvN(M13)_PprpD2-ilvBN and *C. glutamicum* VP_PprpD2-ilvBN The vector pK18mobsacB_PprpD2-ilvB mentioned in Example 1 was transferred by means of electroporation according to a protocol of Liebl et al. (FEMS Microbiology Letters 65, 299-304 (1989)) to the strain *Corynebacterium glutamicum* ATCC14067 and to the valine production strains *Corynebacterium glutamicum* ATCC14067_ilvN (M13) (see Example 4) and *Corynebacterium glutamicum* valine production strain, *C. glutamicum* VPS. The vector pK18mobsacB or pK18mobsacB_PprpD2-ilvB cannot replicate independently in *C. glutamicum* ATCC14067, *C. glutamicum* ATCC14067_ilvN(M13) and *C. glutamicum* VPS and is only retained in the cell if it has integrated into the chromosome as a result of a recombination event. The selection of clones containing integrated pK18mobsacB_PprpD2_ilvB is carried out by plating out the conjugation batch on LB agar (Sambrook et al., Molecular Cloning: A Laboratory Manual, 2nd Ed., Cold Spring Habor, N.Y., 1989), which has been supplemented with 15 mg/l of kanamycin and 50 mg/ml of nalidixic acid. Accreted clones are streaked out on LB agar plates containing 25 mg/l of kanamycin and incubated at 33° C. for 16 hours. For the selection of mutants, in which as a result of a second recombination event the excision of the plasmid has taken place, the clones are cultured non-selectively in LB liquid medium for 20 hours, then streaked out on LB agar containing 10% sucrose and incubated for 24 hours.

The plasmid pK18mobsacB_PprpD2-ilvB as well as the starting plasmid pK18mobsacB contains, in addition to the kanamycin resistance gene, a copy of the sacB gene coding for the levan sucrase from *Bacillus subtilis*. The expression inducible by sucrose leads to the formation of levan-sucrase, which catalyses the synthesis of the product levan toxic to *C. glutamicum*. On LB-agar containing sucrose, therefore, only those clones grow in which the integrated pK18mobsacB_PprpD2-ilvB has in turn been excized. In the case of excision, together with the plasmid either the complete wild-type copy of the ilvB gene including the wild-type promoter region can be excized, or the recombinant copy of the ilvB gene containing the PprpD2 promoter.

Approximately 40 to 50 colonies were tested for the phenotype "growth in presence of sucrose" and "non-growth in the presence of kanamycin". In order to prove that the recombinant PprpD2-ilvB allele has remained in the chromosome, approximately 20 colonies that contain the phenotype "growth in the presence of sucrose" and "non-growth in the presence of kanamycin", were investigated with the aid of the polymerase chain reaction according to the standard PCR method of Innis et al. (PCR Protocols. A Guide to Methods and Applications, 1990, Academic Press). In this connection, a DNA fragment which carries the modified regions of the recombinant PprpD2-ilvB allele was amplified from the chromosomal DNA of the colonies. The following primer oligonucleotides were selected for the proof PCR.

Test Primer 1 (SEQ ID NO: 6)

5'-AAA GCC TGC ATC GCG GAG AC-3'

Test Primer 2 (SEQ ID NO: 7)

5'-TGG TGA TGC CGC GGA TAT CG-3'

The primers make possible the amplification of a DNA fragment about 880 bp in size in clones containing a recombinant PprpD2-ilvBN locus. In clones containing a wild-type PilvBN-ilvBN locus, DNA fragments having a size of about 1136 bp are amplified.

The amplified DNA fragments are identified by means of electrophoresis in a 0.8% strength agarose gel. It was thereby possible to show that the strains carry a modified, recombinant PprpD2-ilvBN allele on the chromosome. The strains were designated as *Corynebacterium glutamicum* ATCC14067_PprpD2-ilvBN, ATCC14067_ilvN(M13) PprpD2-ilvBN and VPS_PprpD2-ilvBN.

EXAMPLE 4

Construction of the Strain *C. glutamicum* ATCC14067_ilvN(M13)

The vector pK18mobsacB_ilvN(M13) mentioned in Example 2 was transferred to the strain *Corynebacterium glutamicum* ATCC14067 by electroporation analogously to the method described in Example 3. The selection of the clones was carried out by the culturing techniques mentioned in Example 3. The detection of positive clones was carried out on the basis of chromosomal DNA, which had been isolated from 20 clones, by amplification of a 947 bp-long product by polymerase chain reaction using the test primers 3 and 4

Test Primer 3 (SEQ ID NO: 15)

5'-CCC AGT AGT CAT CGA CTT C-3'

Test Primer 4 (SEQ ID NO: 16)

5'-CAG CGT CAG CAT CAT AAA GC-3' and subsequent sequencing of the PCR product.

EXAMPLE 5

Performance Test with *Corynebacterium glutamicum* ATCC14067_PprpD2-ilvBN for the Production of L-Valine For the investigation of their ability to produce L-valine, five clones of the strain *Corynebacterium glutamicum* ATCC14067_PprpD2-ilvBN and, as a reference, the strain *Corynebacterium glutamicum* ATCC14067 were pre-cultured in 10 ml of test medium in each case for 16 h at 33° C. For the production test, each 10 ml of test medium were inoculated with the pre-culture obtained, such that the start $OD_{600}$ (optical density at 600 nm) was 0.1. Each clone was tested in three shaker flasks, so that the exemplary strain is represented by a total of fifteen shaker flasks.

The test medium was identical to the CgXII medium described in Keilhauer et al. (Journal of Bacteriology (1993) 175: 5593-5603), but additionally contained 7.5 g/l of yeast extract (Difco (Becton Dickinson GmbH), Heidelberg). The composition of the test medium is summarized in the following Table 1. The test medium for the induction of valine synthesis additionally contained propionate in a concentration of 0.6 g/l (based on the free acid).

TABLE 1

| Component | Content per 1 |
|---|---|
| $(NH_4)_2SO_4$ | 20 g |
| Urea | 5 g |
| $KH_2PO_4$ | 1 g |
| $K_2HPO_4$ | 1 g |
| $MgSO_4 \times 7H_2O$ | 0.25 g |
| 3-Morpholinopropanesulphonic acid (MOPS) | 42 g |
| $CaCl_2$ | 0.01 g |
| $FeSO_4 \times 7H_2O$ | 0.01 g |
| $MnSO_4 \times H_2O$ | 0.01 g |
| $ZnSO_4 \times 7H_2O$ | 0.001 g |
| $CuSO_4$ | 0.0002 g |
| $NiCl_2 \times 6H_2O$ | 0.00002 g |
| Biotin | 0.0002 g |
| Protocatechuic acid | 0.03 g |

TABLE 1-continued

| Component | Content per 1 |
|---|---|
| Dextrose | 40 g |
| Yeast extract | 7.5 g/l |
| pH (using NaOH) | 7 |

The culturing was carried out at 33° C. and 200 rpm in 100 ml shaker flasks. The displacement of the shaker was 5 cm. After 24 and 48 hours, samples were removed from the cultures and the optical density of the content of dextrose and the content of L-valine was determined and the cells were briefly centrifuged off (bench centrifuge type 5415D (Eppendorf) at 13000 rpm, 10 min, room temperature).

The optical density was determined at a wavelength of 660 nm using a GENios microtitre plate photometer (Tecan, Reading UK). The samples were diluted 1:100 with demineralized water before the measurement.

The dextrose was determined using a coupled enzyme test (hexokinase/glucose 6-phosphate dehydrogenase) via NADH formation.

The extracellular amino acid concentrations were determined quantitatively from the culture supernatant by means of reversed phase HPLC (Lindroth et al., Analytical chemistry (1979) 51: 1167-1174). An HPLC apparatus of the series HP1100 (Hewlett-Packard, Waldbronn, Germany) with attached fluorescence detector (G1321A) was used; the system control and the analysis of the data was carried out using an HP Chem-Station (Hewlett-Packard). 1 µl of the amino acid solution to be analyzed was mixed in an automatic pre-column derivatization mit 20 µl of ortho-phthalaldehyde/2-mercaptoethanol ready-to-use reagent (Pierce Europe BV, Oud-Beijerland, Netherlands). The fluorescing, thio-substituted isoindoles resulting here (Jones et al., Journal of Chromatography (1983) 266: 471-482) were separated by means of a combined pre-column (40×4 mm Hypersil ODS 5) and main column (Hypersil ODS 5, both columns from the company CS-Chromatographie Service GmbH, Langerwehe, Germany) using a gradient programme with an increasing non-polar phase (methanol). The polar eluent was sodium acetate (0.1 M; pH 7.2); the flow rate was 0.8 ml per minute. The fluorescence detection of the derivatized amino acids was carried out at an excitation wavelength of 230 nm and an emission wavelength of 450 nm. The valine concentrations were calculated by a comparison with an external standard.

For the calculation of the yield, the amount of L-valine formed was divided by the amount of dextrose consumed.

The results are presented in Table 2 and show that the exemplary strain Corynebacterium glutamicum ATCC14067_PprpD2-ilvBN significantly excretes valine in the presence of propionate in the medium, while without propionate it does not differ from the control strain Corynebacterium glutamicum ATCC14067, which does not significantly produce valine under any condition.

Table 2: L-valine formation after incubation for 24 hours without propionic acid in the medium (Table 2A) or with 0.6 g/l of propionic acid in the medium (Table 2B). Abbreviations: *: ATCC 14067_PprpD2-ilvBN, std. dev.: standard deviation.

TABLE 2A

Results without propionic acid

Time 24 hours

| Strain | Valine g/l (±std. dev.) | Yield g/g (±std. dev.) | OD (±std. dev.) |
|---|---|---|---|
| *_1 | <0.2 | 0 | 26.2 ± 0.8 |
| *_2 | <0.2 | 0 | 26.2 ± 1.7 |
| *_3 | <0.2 | 0 | 26.9 ± 2.2 |
| *_4 | <0.2 | 0 | 27.0 ± 0.5 |
| *_5 | <0.2 | 0 | 26.3 ± 1.8 |
| ATCC 14067 | <0.2 | 0 | 26.6 ± 0.4 |

TABLE 2B

Results with propionic acid

Time 24 hours

| Strain | Valine g/l (±std. dev.) | Yield g/g (±std. dev.) | OD (±std. dev.) |
|---|---|---|---|
| *_1 | 3.04 ± 0.13 | 0.07 ± 0.004 | 24.6 ± 0.3 |
| *_2 | 3.06 ± 0.10 | 0.07 ± 0.003 | 27.5 ± 0.8 |
| *_3 | 2.78 ± 0.06 | 0.07 ± 0.001 | 26.2 ± 0.4 |
| *_4 | 2.93 ± 0.03 | 0.07 ± 0.001 | 27.1 ± 1.4 |
| *_5 | 2.83 ± 0.04 | 0.07 ± 0.001 | 28.1 ± 0.1 |
| ATCC 14067 | <0.2 | 0 | 26.2 ± 4.5 |

EXAMPLE 6

Performance Test Using the Corynebacterium glutamicum-Valine Production Strains

Analogously to Example 5, the strains Corynebacterium glutamicum ATCC14067_ilvN(M13)_PprpD2-ilvBN and Corynebacterium glutamicum VPS_PprpD2-ilvBN were investigated in the shaker flask system.

For the investigation of their ability to produce L-valine, the strain Corynebacterium glutamicum ATCC14067_ilvN (M13)_PprpD2-ilvBN and as a reference the strain Corynebacterium glutamicum ATCC14067_ilvN(M13), or the strain Corynebacterium glutamicum VPS_PprpD2-ilvBN and as a reference the strain Corynebacterium glutamicum VPS, in each case in 10 ml of test medium (Table 3), were pre-cultured at 33° C. for 16 h. For the production test, every 10 ml of test medium were inoculated with the pre-culture obtained such that the start $OD_{600}$ (optical density at 600 nm) was 0.1. Each clone was tested in three shaker flasks, so that the exemplary strain is represented by in total 15 shaker flasks.

TABLE 3

SK1039 was used as the test medium

| | Concentration (g/l) |
|---|---|
| Glucose | 40.0 |
| $(NH_4)_2SO_4$ (100% TDM) | 8.5 |
| $MgSO_4 \cdot 7H_2O$ | 0.85 |
| $KH_2PO_4$ | 0.2 |
| Yeast extract | 1.14 |
| CSL | 10.0 |
| MOPS | 20.0 |
| D-(+)-Biotin 2% | 0.00425 |
| Thiamine HCl | 0.00119 |

TABLE 3-continued

SK1039 was used as the test medium

|  | Concentration (g/l) |
|---|---|
| Fe sulphate 7H$_2$O | 0.003 |
| MnSO$_4$ H$_2$O | 0.003 |
| CaCo3 | 10.00 |

The test medium for the induction of valine synthesis additionally contained propionate in a concentration of 0.6 g/l (based on the free acid).

The culturing conditions, and the determination of the biomass, the dextrose and the valine concentration were carried out analogously as described in Example 5.

The results are presented in Table 4 and show that the valine production strains *Corynebacterium glutamicum* ATCC14067_ilvN(M13)_PprpD2-ilvBN and VPS_PprpD2-ilvBN in the presence of propionate in the medium have a higher specific yield of valine with respect to the carbon source employed than the in each case unmodified starting strains *Corynebacterium glutamicum* ATCC14067_ilvN (M13) and *Corynebacterium glutamicum* VPS.

Table 4: L-Valine yield after incubation for 24 hours without propionic acid in the medium (Table 4A) and with 0.6 g/l of propionic acid in the medium (Table 4B); abbreviations: std. dev.=standard deviation.

TABLE 4A

Results without propionic acid

| Strain | Yield g/g (±std. dev.) |
|---|---|
| ATCC14067_ilvN(M13)_PprpD2-ilvBN | 0.02 ± 0.00 |
| ATCC14067_ilvN(M13) | 0.35 ± 0.01 |
| VPS_PprpD2-ilvBN | 0.02 ± 0.00 |
| VPS | 0.40 ± 0.02 |

TABLE 4B

Results with propionic acid

| Strain | Yield g/g (± std. dev.) |
|---|---|
| ATCC14067_ilvN(M13)_PprpD2-ilvBN | 0.42 ± 0.02 |
| ATCC14067_ilvN(M13) | 0.36 ± 0.01 |
| VPS_PprpD2-ilvBN | 0.45 ± 0.02 |
| VPS | 0.41 ± 0.01 |

EXAMPLE 7

Valine Stability Test for the Strains VPS_PprpD2-ilvBN and VPS

The stability test was carried out in 10 ml liquid cultures (as in Example 6).

Preculturing of the strains VPS and VPS_PprpD2-ilvBN 10 ml of liquid culture in a 100 ml shaker flask (with baffles) were inoculated with 50 µl each of a glycerol continuous culture and incubated for 22 h (33° C., 200 rpm, 5 cm amplitude).

The optical density of the cultures was measured and 1.5 ml of the culture were treated with glycerol (10% glycerol final concentration) and frozen as a cryoculture at −80° C. in a screw cap vessel.

One new 10 ml liquid culture each was inoculated with 50 µl of the cultures and this was incubated again at 33° C. for 22 h with shaking.

This procedure was repeated a further two times, such that each glycerol culture was cultured altogether in four successive liquid cultures. Each culturing corresponds to about 8 cell generations. The four passages in liquid cultures thus correspond altogether to over 30 (ca. 32) cell generations.

Main Culturing of the Strains VPS and VPS_PprpD2-ilvBN

Shaker flask cultures of each continuous culture or cryoculture were inoculated with 10 ml each of liquid medium at a start OD of 0.1. The cultures were subsequently incubated for 24 h. Each culturing was carried out in a duplicate determination. At the end of the incubation (after 24 h), samples were taken for the analysis of the optical density, of the valine titre and of the residual sugar concentration. The analyses were carried out as described under Example 5.

As a result of the performance test (Tab. 5), it is shown that with each passage the valine titre (indicated in relative change in percent), the valine/biomass ratio (indicated in valine/OD) and the yield (g of product formed/g of substrate consumed) for the strain VPS become poorer or lower. This is evidence of the fact that mutations become established in the population, which are negative for the product formation and positive for the biomass formation. After two culturing stages (15.6 generations), the strain VPS already shows a fall-off in the performance data in the test culturing (main culturing results). Thus in a 4-stage process (3 culturing stages+1 production stage) a severe decrease in the performance data (titre, yield, biomass-specific product formation) would be expected. For the strain VPS_PprpD2-ilvBN according to the invention, this negative effect is not seen, however, even on passing through four culturing stages, with more than 30 generations. In contrast to this, the biomass-specific valine formation (valine/OD) even increases slightly. Thus at least a 4-stage production process consisting of 3 culturing stages and of a main culturing is simulated or the requirement is even surpassed.

TABLE 5

Performance data of the stability test (L-valine yield, biomass-specific product formation (valine/OD) and relative changes in the valine formation as a function of the additional cell generations for the control (=0) after incubation for 24 hours (mean values) )

| | Results of the main culturing | | | |
|---|---|---|---|---|
| Strain | Additional cell generations in the culturing track in comparison to the control | Relative change in the valine formation in comparison to the control [%] | Valine/ optical density (OD) | Yield valine/ dextrose Y (P/S) [g/g] [%] |
| VPS_PprpD2-ilvBN (= control) | 0 | 0 | 1.8 | 54% |

TABLE 5-continued

Performance data of the stability test (L-valine yield, biomass-specific product formation (valine/OD) and relative changes in the valine formation as a function of the additional cell generations for the control (=0) after incubation for 24 hours (mean values))

| | | Results of the main culturing | | |
|---|---|---|---|---|
| Strain | Additional cell generations in the culturing track in comparison to the control | Relative change in the valine formation in comparison to the control [%] | Valine/ optical density (OD) | Yield valine/ dextrose Y (P/S) [g/g] [%] |
| VPS_PprpD2-ilvBN_1 | 9 | −3 | 2.1 | 64% |
| VPS_PprpD2-ilvBN_2 | 17 | 6 | 2.8 | 60% |
| VPS_PprpD2-ilvBN_3 | 24 | −5 | 2.3 | 60% |
| VPS_PprpD2-ilvBN_4 | 32 | 3 | 2.4 | 63% |
| VPS (= control) | 0 | 0 | 2.7 | 45% |
| VPS_1 | 7.7 | 2 | 2.9 | 42% |
| VPS_2 | 15.6 | −58 | 2.5 | 48% |
| VPS_3 | 23.4 | −78 | 1.5 | 44% |
| VPS_4 | 31.7 | −85 | 1 | 30% |

FIG. 1: Map of the plasmid pK18mobsacB_PprpD2-ilvB
The abbreviations and designations used have the following meaning.
oriV: ColE1-like origin of pMB1
sacB: the sacB gene coding for the protein levan sucrose
RP4mob: RP4 mobilization site
Kan: Resistance gene for kanamycin
PprpD2: Propionate inducible promoter
'ilvB: 5'-region of the ilvB gene
HindIII: Cleavage site of the restriction enzyme HindIII
EcoRI: Cleavage site of the restriction enzyme EcoRI

---

The invention claimed is:

1. A process for the production of an L-amino acid selected from the group consisting of L-leucine, L-valine and L-isoleucine or of an α-keto acid selected from the group consisting of α-ketoisovalerate, α-keto-methylvalerate and α-ketoisocaproate, said process comprising:
   a) fermenting microorganisms of the genus *Corynebacterium*, wherein:
      i) said microorganisms comprise, in replicable form, a polynucleotide with operator activity, the sequence of which is at least 85% identical to the sequence of position 1 to 121 of SEQ ID NO:1, SEQ ID NO:2 or SEQ ID NO:3 and to which the activator PrpR binds; and
      ii) functionally downstream of the polynucleotide with operator activity, at the 3'-end, are a second polynucleotide having propionate- or 2-methylcitrate-inducible promoter activity; as well as genes ilvB and ilvN encoding for the subunits of an acetolactate synthase, and which regulates the transcription of the genes ilvBN as a function of the addition of the activator PrpR, in a medium;
   b) during the fermenting of said microorganisms, there is a first phase (growth phase), which takes place without inducer, and a second phase during which propionate or 2-methylcitrate is added as an inducer, whereupon the desired L-amino acid or α-keto acid is synthesized under conditions in which the desired L-amino acid or α-keto acid is enriched in the medium and/or in the cells.

2. The process of claim 1, wherein said polynucleotide with operator activity comprises a polynucleotide ("IR 1"), the sequence of which is at least 90% identical to the sequence of position 22 to position 49 of SEQ ID NO:1, SEQ ID NO:2 or SEQ ID NO:3, and also a polynucleotide ("IR 2"), the sequence of which is at least 90% identical to the sequence of position 77 to position 105 of SEQ ID NO:1, SEQ ID NO:2 or SEQ ID NO:3.

3. The process of claim 2, wherein the polynucleotide with operator activity comprises a sequence that is at least 90% identical to the sequence of position 1 to 121 of SEQ ID NO:1, SEQ ID NO:2 or SEQ ID NO:3.

4. The process of claim 2, wherein:
  a) said IR 1 polynucleotide is at least 96% identical to the sequence of position 22 to position 49 of SEQ ID NO:1, SEQ ID NO:2 or SEQ ID NO:3;
  b) said IR 2 the sequence is at least 96% identical to the sequence of position 77 to position 105 of SEQ ID NO:1, SEQ ID NO:2 or SEQ ID NO:3; and
  c) said polynucleotide with operator activity comprises a sequence that is at least 96% identical to the sequence of position 1 to 121 of SEQ ID NO:1, SEQ ID NO:2 or SEQ ID NO:3.

5. The process of claim 1, wherein the polynucleotide with promoter activity comprises a sequence that is at least 90% identical to the sequence of position 122 to 206 of SEQ ID NO:4.

6. The process of claim 1, wherein the polynucleotide with promoter activity comprises a sequence that is at least 98% identical to the sequence of position 122 to 206 of SEQ ID NO:4.

7. The process of claim 1, wherein the gene ilvB codes for a polypeptide, the sequence of which is at least 90% identical to the sequence of SEQ ID NO:9 and the gene ilvN is a polynucleotide codes for a polypeptide, the sequence of which is identical at least 90% identical to the sequence of SEQ ID NO:10.

8. The process of claim 1, wherein the gene ilvB codes for a polypeptide, the sequence of which is at least 98% identical to the sequence of SEQ ID NO:9 and the gene ilvN is a polynucleotide codes for a polypeptide, the sequence of which is identical at least 98% identical to the sequence of SEQ ID NO:10.

9. The process of claim 1, wherein said microorganisms further comprise enzymes of the biosynthetic pathway of the desired L-amino acid or α-keto acid that are amplified and/or metabolic pathways that decrease the formation of the desired L-amino acid or α-keto acid that are at least partially attenuated.

10. The process of claim 1, wherein L-valine is synthesized.

11. The process of claim 1, wherein the *Corynebacteria* employed in the culturing phase go through at least 16 generations and the fermentation comprises at least four stages.

12. The process of claim 11 wherein the *Corynebacteria* employed in the culturing phase go through at least 24 generations and the fermentation comprises at least a shaker flask stage, a PreSeed fermenter stage, a seed fermenter stage and a production fermenter stage.

* * * * *